United States Patent
Godwin et al.

(10) Patent No.: US 6,307,093 B1
(45) Date of Patent: Oct. 23, 2001

(54) ORGANIC COMPOUNDS AND PROCESSES FOR THEIR MANUFACTURE

(75) Inventors: Allen David Godwin, Seabrook, TX (US); Richard Henry Schlosberg, Bridgewater, NJ (US); Frank Hershkowitz, Liberty Corner, NJ (US); Michael G Matturro, Lambertville, NJ (US); Gabor Kiss, Hampton, NJ (US); Kirk Christian Nadler, Brussels; Philippe Louis Buess, Overijse, both of (BE); Richard C Miller, Baton Rouge, LA (US); Paul William Allen, Brussels (BE); Harry William Deckman, Clinton, NJ (US); Raf Caers, Edegem (BE); Edmund John Mozeleski, Califon; Robert P Reynolds, Clinton, both of NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/448,996

(22) Filed: Nov. 24, 1999

Related U.S. Application Data

(62) Division of application No. 08/860,638, filed on Oct. 27, 1997, and a continuation of application No. PCT/EP96/00267, filed on Jan. 17, 1996.

(30) Foreign Application Priority Data

Jan. 18, 1995 (EP) .................................................. 95300301

(51) Int. Cl.$^7$ .................................................. C07C 69/00
(52) U.S. Cl. ........................ 560/129; 560/263; 560/76; 562/512; 568/448; 252/52; 252/56; 252/68; 524/298; 508/485
(58) Field of Search ..................................... 560/129, 263, 560/76; 562/512; 568/448; 252/52, 56, 68; 524/298; 508/485

(56) References Cited

U.S. PATENT DOCUMENTS

| 2,485,989 | 10/1949 | Smith ................................... 260/601 |
| 2,852,563 | 9/1958 | Hagemeyer, Jr. et al. .......... 260/601 |
| 3,445,505 | 5/1969 | Wakamatsu et al. ................. 260/483 |
| 3,527,809 | 9/1970 | Pruett et al. .......................... 260/604 |
| 3,917,661 | 11/1975 | Pruett et al. .......................... 260/410 |
| 4,148,830 | 4/1979 | Pruett et al. .......................... 260/604 |
| 4,270,006 | 5/1981 | Heilen et al. ......................... 568/396 |
| 4,426,542 | 1/1984 | Barker et al. ........................ 568/883 |
| 4,543,420 | 9/1985 | Godwin et al. ........................ 560/76 |
| 5,391,311 | 2/1995 | Ishida et al. ............................ 252/52 |
| 5,997,760 | 12/1999 | Schlosberg et al. .................... 252/68 |

FOREIGN PATENT DOCUMENTS

| 0 013 385 A 1 | 7/1980 | (EP) . |
| 0 452 816 A2 | 10/1991 | (EP) . |
| 2249061 | 5/1975 | (FR) . |
| 1 547 856 A | 6/1979 | (GB) . |
| 2 059 419 A | 4/1981 | (GB) . |

OTHER PUBLICATIONS

"The Nonyl Phthalate Ester and its Use in Flexible PVC," B.L. Wadey et al., Journal of Vinyl Technology, vol. 12, No. 4, pp. 208–211, Dec. 1990.

"New Syntheses with Carbon Monoxide," Edited by J. Falbe, Springer–Verlag Berlin Heidelberg New York, 1980.

"The Rhodium–Promoted Guerbet Reaction," Patrick L. Burk, et al., Journal of Molecular Catalysis, 1:14, pp. 1–21, 1985.

"Inorganic Syntheses," George W. Parshall, vol. XV, pp. 58–60, 1980.

"Synthesis of methyl 2D,4D,6D–, 2D,4L,6D–,2L,4D,6D– and 2L,4L, 6D–trimethylnonanoate," Goran Odham, Arkiv for Kemi Band 27 nr 21, pp. 231–250, Mar. 8, 1967.

"Compendium of Organic Synthetic Methods," Ian T. Harrison et al., Wiley–Interscience, Section 108, pp. 280–286, 1971.

"1,3,5,7–Tetramethyldecyl Formate, Lardolure: Aggregation Pheromone of the Acarid Mite, *Lardoglyphus konoi* (Sasa et Asanuma) (Acarina: Acaridae)," Yasumasa Kuwahara et al., Agric. Biol. Chem., 46, (9), pp. 2283–2291, 1982.

"Structural Characterization of Exxal® Alcohols," Exxon Chemical S–3022–MJG.0389, Mar. 31, 2000.

*Primary Examiner*—Sreeni Padmanabhan
(74) *Attorney, Agent, or Firm*—Douglas J. Collins

(57) ABSTRACT

Esters of branched $C_9$ alcohols suitable as plasticizers are formed by esterification of a $C_9$ alcohol produced by the aldol condensation from propanal and a $C_6$ aldehyde and hydrogenation, the propanal optionally having been made from natural gas streams.

23 Claims, 7 Drawing Sheets

PROCESS EMBODIMENT WITH TWO ALDOL REACTORS

ORGANIC COMPOUNDS AND PROCESSES FOR THEIR MANUFACTURE

This application is a divisional application of pending application Ser. No. 08/860,638, filed Oct. 27, 1997 which is a continuation of PCT/EP96/00267 filed Jan. 17, 1996.

FIELD OF THE INVENTION

This invention relates to a process for the manufacture of aldehydes, alcohols, acids, and their derivatives. The invention also relates to the uses of the compounds, especially to the use of the alcohols and their derivatives, to the uses of the esters, both of the alcohols and acids, and of salts of the acids. More especially, the invention relates to the use of esters as synthetic lubricants and as plasticizers, to polymeric compositions plasticized by the esters, and to products made from the compositions. Certain of the compounds are novel.

BACKGROUND OF THE INVENTION

The esters of 2-ethylhexanol, especially the phthalate, are among the most commonly used plasticizers. The alcohol is obtainable by, for example, subjecting propene to hydroformylation, dimerizing the resulting butanal by the aldol reaction, a term which is used throughout this specification, including the claims, as including the subsequent dehydration to an unsaturated aldehyde, and hydrogenating the resulting aldehyde to form a saturated alcohol.

The propene, produced for example by a steam cracking plant, has to be purified before hydroformylation, and its cost as feedstock is increased as a result.

Although the plasticizer esters derived from 2-ethylhexanol are widely used, for some purposes, for example where a lower volatility, or a stronger solvator for the polymer is needed, higher molecular weight esters, for example those based on nonanol, are preferred. The $C_9$ esters presently available commercially are typically derived from an isomeric mixture of $C_9$ alcohols and the users' requirements for product consistency may result in manufacturing complexities.

These complexities result from variations in feed composition and reaction conditions in the process for the manufacture of the precursors to the alcohols. These precursors may be formed for example by oligomerizing a mixed $C_3$ to $C_5$ olefin feed, giving a mixture of linear and branched olefins, predominantly having six to ten carbon atoms, from which is distilled a mixed $C_8$ olefin, which is in turn hydroformylated (oxonated) and hydrogenated to form the isomeric $C_9$ alcohol mixture.

In other commercial processes, the $C_9$ alcohol precursors are typically obtained by-dimerizing butene streams and oxonating the resulting $C_8$ olefin fraction. The butene stream itself contains a mixture of isomers, in proportions that may vary over a period, and the cobalt oxo process causes some isomerization. Thus the alcohols resulting from hydrogenation of the aldehyde form a reaction product of variable isomer distribution together with lower and higher homologues, necessitating further treatment if customers' product specifications are to be met.

In a typical commercial process for the manufacture of a plasticizer ester, the alcohol is employed in excess over the acid, and alcohol is stripped from the ester product and recycled. Any impurities and any less reactive isomers tend to concentrate in the reaction vessel as the reaction progresses, resulting in a change in the composition over time. In turn, the downstream users' quality control inspection of the incoming product is more onerous than if it were a single isomer.

Processing of thermoplastics containing a multi-isomer plasticizer may be more difficult to control in certain applications, resulting in a greater possibility of inconsistencies in properties between different batches of the final product.

This in turn may require the user to have tighter control over process variables, e.g., oven temperature ranges in motor vehicle paintshops and flooring material lines, than would otherwise be necessary, and also complicates material recycling.

In applications employing the corresponding acids, there is an even greater requirement for purity, for example when the acids are being employed in synthetic lubricant manufacture, or in peroxide polymerization initiator manufacture.

Finally, effluent and environmental monitoring is more difficult; e.g., a single isomer material may have a minimum detectability an order of magnitude lower than a multi-isomer material.

There accordingly remains a need for an alternative route to commercially useful organic molecules, and more especially one that provides flexibility and a greater control of product structure, particularly the ability to produce single isomers if desired.

In addition there remains a need for a route sufficiently flexible to be able to use different feedstocks of varying purity, particularly feedstocks from the various natural gas sources emerging around the world.

BRIEF SUMMARY OF THE INVENTION

The present invention provides a process for the manufacture of a saturated aliphatic $C_9$ aldehyde which comprises subjecting a $C_6$ aldehyde to an aldol condensation with propanal to form an unsaturated $C_9$ aldehyde and hydrogenating the $C_9$ aldehyde to form a saturated $C_9$ aldehyde.

Optionally, the saturated $C_9$ aldehyde is hydrogenated further to the corresponding alcohol, which is optionally esterified, or the $C_9$ aldehyde may be oxidized to the corresponding acid. If desired, however, the unsaturated $C_9$ aldehyde may instead be hydrogenated in a single stage to the saturated alcohol (in which process the saturated aldehyde is typically formed as an intermediate but not isolated), to a mixture of saturated aldehyde and alcohol, or to an unsaturated alcohol.

The saturated $C_6$ aldehyde may be obtained, for example, as will be described in more detail below, from a composition containing a $C_2$ unsaturated hydrocarbon and/or synthesis gas (CO & $H_2$) obtainable, for example, by conversion of a natural gas stream. A stream containing both these components may be subjected to hydroformylation conditions, and the resulting propanal-containing composition subjected to aldolization, the resulting hexenal (which is largely a single isomer) being hydrogenated to form the starting $C_6$ saturated aldehyde, the last-mentioned steps or the latter step being carried out, if desired, in conjunction with the aldol condensation to form a $C_9$ aldehyde.

As a further route to a saturated $C_6$ aldehyde, a synthesis gas stream may be subjected to the Fischer-Tropsch process, to yield, when a cobalt catalyst is used primary alcohols and, when an iron catalyst is used, inter alia, linear α-olefins. These products may be dehydrogenated and oxonated, respectively, to give mainly normal aldehydes. Other routes include oxonation of a pentene, and the formation of Ziegler alcohols by catalytic treatment of ethylene to form a range of higher alcohols and dehydrogenation to aldehydes. Separation of the desired carbon number material may take place at any suitable stage in these processes.

The present invention also provides a process comprising
(a) subjecting a composition comprising a $C_2$ unsaturated hydrocarbon, carbon monoxide and hydrogen to hydroformylation conditions to form a propanal-containing composition,
(b) subjecting the propanal-containing composition to first and second aldol condensations, causing trimerization to an unsaturated $C_9$ aldehyde and, optionally,
(c) hydrogenating an intermediate unsaturated C6 aldehyde resulting from the first aldol condensation to a saturated $C_6$ aldehyde and, optionally,
(d) hydrogenating the $C_9$ aldehyde to a saturated aldehyde, the $C_9$ aldehyde being the doubly unsaturated product of step (b), the singly unsaturated product resulting from aldol condensation of the product of step (c) with a further propanal molecule, or a mixture of the product of step (b) and the said-singly unsaturated product and, optionally,
(e) oxidizing the product of step (d) to form a $C_9$ acid or optionally
(f) hydrogenating the product of step (b) or step (d) to form a saturated $C_9$ alcohol and, optionally,
(g) esterifying the saturated $C_9$ alcohol resulting from step (f).

The invention further provides a process comprising
(b) subjecting a propanal-containing composition to first and second aldol condensations, causing trimerization to an unsaturated $C_9$ aldehyde,
(c) hydrogenating an intermediate unsaturated C6 aldehyde resulting from the first aldol condensation to a saturated $C_6$ aldehyde, step (c) being optional, and
(d) hydrogenating the $C_9$ aldehyde to a saturated aldehyde, the $C_9$ aldehyde being the doubly unsaturated product of step (b), the singly unsaturated product resulting from aldol condensation of the product of step (c) with a further propanal molecule or a mixture of the product of step (b) and the said singly unsaturated product and, optionally,
(e) oxidizing the product of step (d) to form a $C_9$ acid or, optionally
(f) hydrogenating the product of step (b) or step (d) to form a saturated $C_9$ alcohol and, optionally,
(g) esterifying the saturated $C_9$ alcohol resulting from step (f).

The invention still further provides a process comprising
(b) subjecting a propanal-containing composition to a first aldol condensation,
(c) hydrogenating the unsaturated $C_6$ aldehyde resulting from the first aldol condensation to a saturated $C_6$ aldehyde, subjecting the resulting saturated $C_6$ aldehyde to a second aldol condensation with propanal to form an unsaturated $C_9$ aldehyde,
(d) hydrogenating the $C_9$ aldehyde to a saturated aldehyde and either
(e) oxidizing the product of step (d) to form a $C_9$ acid or
(f) hydrogenating the product of step (d) to form a saturated $C_9$ alcohol, optionally
(g) esterifying the saturated $C_9$ alcohol resulting from step (f).

The $C_6$ unsaturated aldehyde referred to above in the process in which propanal is dimerized will largely be 2-methyl-2-pentenal; the $C_6$ saturated aldehyde resulting from its hydrogenation will be 2-methylpentanal; the doubly and singly unsaturated, and saturated, $C_9$ aldehydes will be 2,4-dimethyl-2,4-heptadienal, 2,4-dimethyl-2-heptenal, and 2,4-dimethylheptanal respectively, the saturated $C_9$ alcohol will be 2,4-dimethylheptanol, and the $C_9$ acid will be 2,4-dimethylheptanoic acid, but other isomers of the $C_9$ materials may be formed in small quantities.

Alternatively, from the unsaturated $C_9$ aldehydes there may be made the corresponding 2,4-dimethyl-2,4-heptadienol and 2,4-dimethyl-2-heptenol by, for example, hydrogenation in the presence of a catalyst comprising platinum with zinc or iron salts, or in the presence of an iridium/carbon or osmium/carbon catalyst, as described in Houben-Weyl, Band IV, Section IC, pp 218 and 224 and the literature referred to therein.

In J. Vinyl Technology, 1990, 12(4), 208 ff, B. L. Wadey et al describe the properties of six dinonyl phthalates, of which two, di-n-nonyl and di(1-methyloctyl) phthalates, were prepared for the study and four are stated to be the four produced commercially as plasticizers. One of these, identified by the terminology JDP, is clearly intended to represent the plasticizer sold by an affiliate company of the present applicants under the trade mark Jayflex DINP. This plasticizer ester is derived from an alcohol mixture containing a substantial proportion of dimethylheptanol isomers, but which actually contains less than 4% of 2,4-dimethylheptanol together with 20 or more other isomers. It appears, therefore, that the characterization at one point in the Wadey et al paper of JDP as 2,4-dimethylheptyl 4,6-dimethylheptyl phthalate is merely schematic. There is, moreover, no commercially economic process that could make that individual ester alone or isolate it from an isomeric mixture.

DESCRIPTION OF THE RELATED ART

In U.S. Pat. No. 2852563 (Hagemeyer, et al) there is disclosed a process in which unsaturated aldehydes are prepared from an α-carbon atom branched aldehyde and an aldehyde unbranched at the α-carbon atom by aldol condensation. Saturated aldehydes and alcohols are produced by hydrogenation of the resulting unsaturated aldehydes, and plasticizers are made by esterifying the alcohols. Exemplary of the esters is the phthalate ester of 2-propyl-4-methylhexanol.

In U.S. Pat. No. 2,485,989 (Smith, et al), aldol condensation of butanal and hydrogenation of the product to the saturated aldehyde 2-ethylhexanal are carried out simultaneously.

Similarly, in U.S. Pat. No. 4,270,006 (Heilen et al) hydrogenation of the double bond in the product aldehyde is carried out simultaneously with the aldol reaction, using a Group VIII/rare earth metal catalyst combination. In an example, propanal is converted predominantly to 2-methylpentanal, with small proportions of 2,4-dimethylhepta-2,4-dienal and of 2,4-dimethylhept-2-enal also being produced.

British specification No. 1547856 (Grace) describes the use of a phase transfer catalyst (PTC) in aldol condensations, the products of which are subsequently hydrogenated to form alcohols which may be esterified to form base stocks for lubricants. In an example, the reaction of 2-ethylhexanal, which itself may be made by aldol condensation of n-butyraldehyde and hydrogenation, with n-butyraldehyde is carried out with and without a PTC. In the presence of the PTC, 89% of the ethylhexanal that had reacted was converted to the desired 2,4-diethyloctenal; in its absence the corresponding figure was 45%.

DETAILED DESCRIPTION OF THE INVENTION

Surprisingly, in view of the disclosure in GB-A-1547856 discussed above, the unsaturated $C_9$ aldehydes may be produced by the present invention with good selectivity from propanal in the absence of a phase transfer catalyst, although the use of a PTC is not excluded from the present invention. The presence of a PTC in the reaction which is generally carried out in a multiphase mixture with the removal by evaporation or phase separation of the water produced in the reaction complicates the recovery of the desired product from the reaction mixture.

The composition treated in step (a) of one aspect of the present invention comprises, as indicated above, as essential ingredients carbon monoxide, hydrogen, and one or both $C_2$ unsaturated hydrocarbons. In certain embodiments of the invention, the hydrocarbon is desirably ethylene, and acetylene is advantageously absent or present in very small proportions. In other embodiments, the essential hydrocarbon is ethylene and the presence of acetylene is optional or even advantageous.

The composition may be obtained by numerous methods, including mixing pure $C_2H_4$, CO and $H_2$, mixing purified commercially produced $C_2H_4$ with purified synthesis gas (syngas) or as the product of a partial oxidation (POX) or steam reforming unit, mixed with the product from a steam or catalytic cracking furnace, which product may be purified or may merely have had catalyst poisons removed but be otherwise untreated. The composition is, however, conveniently a dilute multi-component syn gas (DMCS) stream, by "dilute" being meant that the stream has not been completely purified by the removal, for example, by cryogenic separation, of diluents, e.g., methane and ethane, that do not take part in the hydroformylation reaction. The stream may result from treatment of natural gas, e.g., from the mixture of one stream containing CO and $H_2$ produced by conventional POX technology or steam or catalytic reforming and a second stream containing ethylene and acetylene obtained by methane pyrolysis, as described in more detail in U.S. patent application Ser. No. 375,324 of Jan. 18, 1995, and a corresponding PCT application entitled "Direct Hydroformylation of a Multi-Component Synthesis Gas Containing Carbon Monoxide, Hydrogen, Ethylene and Acetylene", applicants Gabor Kiss et al., assigned to Exxon Research & Engineering Company, filed simultaneously with the present application, and whose entire disclosures are incorporated by reference herein.

Depending on the source, the DMCS will contain, as indicated above, $H_2$, Co and one or both $C_2$ unsaturated hydrocarbons, and in addition different neutral and undesired species.

In certain embodiments, the DMCS will also contain one or more $C_{3+}$ mono- or poly-olefinically unsaturated hydrocarbons, more especially $C_3$ to $C_5$ mono- or poly-olefins, and more especially will contain, in addition to the $C_2$ unsaturates, propene and butenes. By this means, the composition of the resulting aldol product may be controlled to contain a mixture of $C_9$ species with, more especially, some $C_{10}$ and $C_{11}$ species, in addition to any $C_{12}$ species resulting from tetramerization of the propanal. The proportion of other species, largely $C_{10}$ species, is advantageously at most 25%, and preferably in the range of 10 to 20%, by weight, based on the total weight of product, resulting in a final plasticizer ester product having lower volatility and enhanced permanence in polymeric compositions.

If desired, at least part of the $C_{10+}$ species may be separated, enabling use of the alcohols as such or in derivative form, e.g., in synthetic lubricants or plasticizers.

The DMCS composition, as far as concerns neutral and essential components, is advantageously as follows in molar terms:

CO: 1 to 50%, preferably 1 to 35%, of gas.

$C_2H_4/C_2H_2$: total up to 100% of Co.

$H_2$: from, at minimum, the molar equivalent of the ethylenically unsaturated species plus twice that of the acetylenically unsaturated species, to a maximum of 60% of DMCS. A preferred maximum is twice the molar equivalent of ethylenically unsaturated species plus three times that of acetylenically unsaturated species. Exceptionally, if the proportion of acetylene is so low that there is no economic advantage in its conversion, the minimum hydrogen content may be the molar equivalent of the ethylenically unsaturated species.

Sum of alkanes, $CO_2$, $N_2$, and $H_2O$: 0 to 70%, preferably 0 to 40%.

Certain trace components of the multicomponent syngas feed are known to be detrimental in the oxo reaction. Some are irreversible catalyst poisons, e.g., sulphur compounds, for example, $H_2S$ and COS. Others, for example, halides, cyanides, and iron carbonyls, cause reversible poisoning or accelerated catalyst deactivation, or unwanted reactions in downstream processing. The concentration of the detrimental components may be adjusted by a variety of techniques known per se, to provide an acceptable multicomponent syngas feed to the oxo reactor.

As described in more detail in the above-identified co-pending U.S. and PCT applications, the literature contains many references to hydroformylation of pure ethylene and to hydroformylation of pure acetylene with syngas; literature sources include "New Syntheses with Carbon Monoxide", Ed. J. Falbe, Springer Verlag, New York, 1980, especially the Chapter "Hydroformylation, Oxo Synthesis, Roelen Reaction" by B. Cornils; and U.S. Pat. Nos. 3527809, 3917661 and 4148830, which describe an oil soluble phosphine-modified rhodium catalyst, especially useful with ethylene; the disclosures of all these documents are incorporated herein by reference. The presence of acetylene causes difficulties however, and the literature cited in the U.S. application generally treats acetylene as a component to be avoided. According to the present invention, the hydroformylation of substantially acetylene-free compositions may be effected under hydroformylation conditions known per se, using a catalyst known per se, for example, any group VIII transition metal catalyst, especially Co and Rh, while hydroformylation of acetylene-containing (as well as substantially acetylene-free) compositions is advantageously carried out using as catalyst an oil-soluble rhodium complex comprising a low valence Rh complexed both with carbon monoxide and a triorganophosphorus compound. As triorganophosphorus compound there may be mentioned, for example, one or more oil-soluble triarylphosphines, trialkylphosphines, alkyl-diarylphosphines, aryl-dialkylphosphines, triorganophosphites, especially trialkylphosphites and triarylphosphites (in which list alkyl includes cycloalkyl), containing one or more phosphorus atoms per molecule capable of complexation with Rh by virtue of having a lone pair of electrons on the phosphorus. Instead of, or in addition to, such monodentate compounds, a bidentate phosphorus compound may be used as ligand. Triorganophosphorus ligands which are known to provide good catalytic activity in the hydro-formylation of pure olefin feeds are suitable for the use in the process of the present invention, their concentration preferably being such that (a) the molar P/Rh ratio is at least 2:1, the minimum preferred ratio depending on the nature of the phosphorus-containing ligand, for example the minimum preferred ratio being 2:1 for a bidentate ligand and 4:1 for a phosphite ligand, most preferably the ratio being at least 30:1; (b) the total concentration of the coordinately active phosphorus is at least 0.01 mol/l; and (c) the $[P]/p_{co}$ ratio maintained in the reactor is at least 0.1 mmol/l/kPa, where [P] is the total concentration of the coordinately active phosphorus in the solution, and $p_{co}$ is the partial pressure of carbon monoxide in the gas phase.

As examples of the ligands there may be mentioned trioctylphosphine, tricyclohexylphosphine, octyldiphenylphosphine, cyclohexyldiphenylphosphine, phenyldioctylphosphine, phenyldicyclohexylphosphine, triphenylphosphine, tri-p-tolylphosphine, trinaphthylphosphine, phenyl-dinaphthylphosphine, diphenylnaphthylphosphine, tri-(p-methoxyphenyl) phosphine, tri-(p-cyanophenyl)phosphine, tri-(p-nitrophenyl)phosphine, and p-N,N-dimethylaminophenyl (diphenyl)phosphine, trioctylphosphite or tri-p-tolylphosphite; as bidentate compound there may be mentioned diphos-bis(diphenylphosphino)ethane.

Advantageously, the Rh concentration in the reaction mixture is in the range from $1\times10^{-5}$ to $1\times10^{-2}$ moles/liter or, in effect, in the range from 1 to 1000 ppm, preferably 20 to 500 ppm, based on the total weight of the solution.

The catalyst is advantageously contacted with feed containing acetylene and/or ethylene in a solution of the catalyst in an oily solvent or a mixture of such solvents, for example aliphatic and aromatic hydrocarbons (e.g., heptanes, cyclohexane, toluene), esters (e.g., dioctyl phthalate), ethers, and polyethers (e.g., tetrahydrofuran, and tetraglyme), aldehydes (e.g., propanal, butanal) the condensation products of the oxo product aldehydes or the triorganophosphorus ligand itself (e.g., triphenylphosphine).

Rhodium may be introduced into the reactor either as a preformed catalyst, for example, a solution of hydridocarbonyl tris(triphenylphosphine) rhodium(I) or it may be formed in situ. If the catalyst is formed in situ, the Rh may be introduced as a precursor such as acetylacetonatodicarbonyl rhodium(I) $\{Rh(CO)_2(acac)\}$, rhodium oxide $\{Rh_2O_3\}$, rhodium carbonyls $\{Rh_4(CO)_{12}, Rh_6(CO)_{16}\}$, tris (acetylacetonato) rhodium(I), $\{Rh(acac)_3\}$, or a triaryl phosphine-substituted rhodium carbonyl $\{Rh(CO)_2(PAr_3)\}_2$, wherein Ar is an aryl group.

Hydroformylation is advantageously conducted at a temperature in the range from 40 to 200° C., more advantageously from 80 to 180° C., and preferably from 90 to 155° C.

The reaction is advantageously conducted at a pressure in the range of 0.05 to 50 MPa (absolute), and preferably in the range of about 0.1 to 30 MPa with a partial pressure of carbon monoxide advantageously not greater than 50% of the total pressure. For safety reasons, the acetylene partial pressure should be limited to a maximum of 0.2 MPa.

Advantageously, the proportions of carbon monoxide, hydrogen, ethylene, and acetylene in the feed to the oxo reactor at the foregoing pressures are maintained as follows: CO from about 1 to 50 mol % preferably about 1 to 35 mol %; $H_2$ from about 1 to 98 mol %, preferably about 10 to 90 mol %; ethylene and acetylene individually and in combination from about 0.1 to 35 mol %, preferably about 1 to 35 mol %.

The reaction may be conducted either in a batch mode or, preferably, on a continuous basis. In a continuous mode a residence time of up to 4 hours may advantageously be used, with a preferred residence time being in the range of from ½ to 2 hours.

Since the current commercial catalytic oxo conversion process takes place in the liquid phase and the reactants are gaseous compounds, a high contact surface area between the gas and liquid phases is desirable to avoid mass transfer limitations. A high contact surface area between the catalyst solution and the gas phase may be ensured in any suitable manner, for example, by stirring in a batch autoclave operation. In a continuous operation the reactor feed gas can be contacted with the catalyst solution in, for example, a continuous-flow stirred autoclave where the gas is introduced and dispersed at the bottom of the vessel, preferably through a perforated inlet. Good contact between the catalyst and the gas feed may also be ensured by dispersing the solution of the Rh catalyst on a high surface area support, a technique well known in the art as supported liquid phase catalysis.

Especially when the feed composition contains both acetylene and ethylene, different stages of hydroformylation may be carried out under different conditions, more severe (e.g., higher temperature or catalyst or ligand concentration) conditions being used for acetylene conversion than for ethylene. This may be achieved by the use of two or more reactors in series, with an increase in severity as the feed moves from one reactor to the next or, in the case of a plug flow reactor, a temperature increase with travel downstream along the length of the plug flow reactor. Such multistage operation may be used even if acetylene is not present in the composition.

The propanal used as a reactant in the aldolization step or steps of the processes according to the invention may be obtained, as in some embodiments above, by oxonation of a $C_2$ unsaturated hydrocarbon. If desired, oxonation may be carried out under conditions yielding propanol, which may be condensed and dehydrated to yield a desired $C_6$ aldehyde by the Guerbet reaction, described in Burk et al., J. Mol. Cat., 33(1) 1–21.

In other embodiments, the propanal may be obtained by other means, for example, by dehydrogenation of propanol, e.g., over a copper catalyst, hydrogenation of acrolein, bio-oxidation of propane, partial oxidation of propanol, whether resulting from bio-oxidation or otherwise obtained, e.g., oxidation with air, or ozonation of 1-butene.

The condensation of two molecules of an aldehyde to form an aldol, usually followed immediately by dehydration, to form an unsaturated aldehyde with twice the original number of carbon atoms (or the sum of the carbon atoms of two different aldehydes in a cross-aldolization) is well known, as are the conditions required to effect the condensation. In general, the reactants may be either in the vapour or liquid phase, at moderately elevated temperatures, e.g., from 40° C. to 200° C., and pressures, e.g., from 0.01 to 2 MPa, preferably from 0.1 to 2 MPa. The reaction is generally carried out in the presence of a catalyst, which may be solid or liquid, and either acidic or, preferably, basic. Although organic, bases may be used, a, preferably strong, inorganic base, for example an alkali metal hydroxide or carbonate, is preferred, advantageously in the form of an aqueous solution. In other embodiments a solid catalyst, e.g., a metal oxide, especially a titanium or magnesium oxide, may be used. The above conditions apply generally to the aldol process steps of the present invention; under the preferred conditions dehydration is very fast and essentially complete.

The desired saturated $C_9$ aldehyde and its successor molecules advantageously have the hydrocarbon skeleton of 2,4-dimethylheptane. In order to maximize the yield of the desired $C_9$ product, it has been found advantageous to hydrogenate the 2-methyl-2-pentenal to 2-methylpentanal between the first and second aldol condensations. Selective hydrogenation of the unsaturation leaving the carbonyl group unaffected may be carried out in the gas/liquid or gaseous phase using any of the catalysts known per se for that purpose. As examples of suitable hydrogenation catalysts, there may be mentioned palladium, e.g., a supported palladium catalyst, using, for example, an alumina or carbon support, under relatively mild conditions, e.g., a hydrogen pressure of up to 3, preferably between 0.5 and 2.0, MPa, and a temperature within the range of 80 to 200° C., optionally in an inert solvent. Suitable solvents include aliphatic, alicyclic and aromatic hydrocarbons or oxygenated solvents, for example, alcohols, esters and ethers.

The second aldol condensation, reacting propanal either with 2-methyl-2-pentenal or, preferably, with 2-methylpentanal, may be carried out under conditions similar to the first condensation.

If it is desired to make the saturated $C_9$ aldehyde 2,4-dimethylheptanal from the immediate product of the second aldolization, 2,4-dimethyl-2,4-heptadienal or, preferably, 2,4-dimethyl-2-heptenal, further hydrogenation may be effected as described above for the manufacture of the saturated $C_6$ aldehyde. This procedure is conveniently also used if the desired end-product is the corresponding 2,4-dimethylheptanoic acid.

If, however, the desired product is the saturated alcohol 2,4-dimethylheptanol then more vigorous hydrogenation conditions may if desired be employed, hydrogenation of the ethylenic unsaturation and reduction of the carbonyl group taking place at the same time. For this purpose, the reaction may be carried out under conditions and in the presence of catalyst systems known per se. For example, the catalyst may be Ni, Raney Ni, Pt or Pd, partially reduced copper oxides, copper/zinc oxides, copper chromite, the copper-based catalyst advantageously being used in combination with cobalt or nickel catalysts; Ni/Mo; Co/Mo or Mo on carbon, optionally in their sulphided form. Any of the above catalysts may be used alone or in combination; nickel is the preferred catalyst. The conditions may include, for example, a hydrogen pressure from 2 to 30 MPa and a temperature in the range of 100 to 240° C.

If it is desired to maintain a number of options for the use of the saturated $C_9$ aldehyde, the present invention also provides for a two-stage hydrogenation of the unsaturated aldehyde, the first stage being carried out in the presence of a mild catalyst, for example, a palladium catalyst as mentioned above, in a first reactor, yielding the saturated aldehyde. This may be further hydrogenated using one of the stronger catalysts mentioned above, for example, Ni, in a second reactor. Alternatively, the saturated aldehyde may be oxidized, or further aldolized, e.g., with propanal to yield a $C_{12}$ aldehyde, the production of which aldehyde, both by the above route or by dimerization of the $C_6$ aldehyde, and its derivatives, also being provided by the invention.

This procedure has the advantage, in addition to flexibility, of facilitating better control of the hydrogenation reaction which, if carried out in a single reactor from unsaturated aldehyde to saturated alcohol, may give an excessive temperature increase because of the heat released on simultaneous hydrogenation of two bonds. The need to control such a highly exothermic reaction adds to reactor costs.

Oxidation of the saturated aldehyde to the corresponding carboxylic acid may be carried out by any method known per se, i.e., practised in the art or described in the literature. Oxidation is conveniently carried out using oxygen, if desired or required in the presence of a catalyst. As catalyst there may be mentioned a solution containing metallic cations, e.g., copper, cobalt or manganese.

When the hexanal to be subjected to aldolization to form a $C_9$ aldehyde is 2-methylpentanal it may be, as in a number of embodiments of the invention, most readily obtained by aldol condensation of propanal and hydrogenation of the unsaturation in the resulting hexenal. That hexanal may, in other embodiments, be obtained by that or other routes.

In still further embodiments, however, other hexanals may be employed. For example, a normal $C_6$ aldehyde may be obtained from synthesis gas by the Fischer-Tropsch process, hydration of the resulting alkane to alkanol and dehydrogenation to alkanal. Other routes to normal hexanal include hydration of a $C_6$ α-olefin, oxonation of $C_5$ Ziegler olefins, and fat-splitting of a coconut or palm kernel oil alcohol, followed by dehydrogenation. Cross-aldolization of the n-hexanal yields a mixture of isomeric nonenals, including 2-methyl-2-octenal and 2-butyl-2-pentenal, which may be hydrogenated to the corresponding saturated aldehydes, which may in turn be further hydrogenated to the corresponding saturated alcohols, including 2-methyl-octanol or 2-propylhexanol, if desired in a combined process, or oxidized to the corresponding acids, including 2-methyloctanoic acid and 2-propylhexanoic acid. Alternatively the nonenals may be hydrogenated to the corresponding unsaturated alcohols, including 2-methyl-2-octenol and 2-butyl-2-pentenol.

The reaction sequence described above with reference to formation of a $C_9$ material from propanal may be carried out in a number of different ways, for example:

In a first embodiment of the trimerization sequence, dimerization of propanal is carried out in a first aldolization zone, the unsaturated product is selectively hydrogenated to 2-methylpentanal in a first hydrogenation zone, the resulting dimer product and further propanal being condensed in a second aldolization zone, the trimer reaction product and any remaining dimer are separated, the trimer being hydrogenated in a second hydrogenation zone either to the saturated aldehyde or the saturated alcohol, as desired, and remaining dimer returned to the first hydrogenation zone.

In a variation of this embodiment, dimerization of propanal is carried out in a first aldolization zone, the unsaturated product is selectively hydrogenated to 2-methylpentanal in a first hydrogenation zone, the resulting dimer product and further propanal are condensed in a second aldolization zone, the trimer is hydrogenated, in the presence of any remaining dimer, in a second hydrogenation zone to the saturated aldehyde, the trimer and any remaining diner are separated, remaining dimer is returned to the second aldolization zone and, if desired, the saturated aldehyde is hydrogenated in a third hydrogenation zone to the saturated alcohol.

In a second embodiment, a single aldolization zone is provided, in which zone both dimerization of propanal and reaction of propanal with 2-methylpentanal to form an unsaturated trimer are carried out, the mixed reaction product is separated into a $C_9$-comprising component and a dimer-comprising component, the dimer-comprising component being passed to a first hydrogenation zone where unsaturated dimer is selectively hydrogenated to 2-methylpentanal, the product from the first hydrogenation zone being returned to the aldolization zone, the $C_9$-comprising component being hydrogenated in a second hydrogenation zone either to the saturated aldehyde or the saturated alcohol as desired.

In a variation of this embodiment, the mixed reaction product from the aldolization zone is passed to a first hydrogenation zone where unsaturated dimer and trimer are selectively hydrogenated to saturated dimer and trimer aldehydes, the mixed saturated aldehydes are separated into a dimer-comprising component and a trimer-comprising component, the dimer-comprising component being returned to the aldolization zone, and the trimer-comprising component is, if desired, hydrogenated in a second hydrogenation zone to the saturated alcohol.

In both the first and second embodiments, the dimer aldehyde, after being separated from the trimer or $C_9$ reaction product, may if desired be further separated into saturated and unsaturated $C_6$ aldehydes, only the unsaturated component being returned to the first hydrogenation zone, the saturated component being returned to the, or the second, aldolization zone. Provided, however, that conditions in the first hydrogenation are such that saturated aldehyde is not further hydrogenated to alcohol, the saturated aldehyde may with advantage be returned without separation to the first hydrogenation zone where it acts as an inert diluent to assist in temperature control; where there are two aldolization zones, saturated aldehyde may, if desired, be returned to the first zone.

In a third embodiment, a multipurpose reaction zone is provided, in which aldolization of propanal, selective hydrogenation of 2-methyl-2-pentenal to 2-methylpentanal, and aldolization of 2-methylpentanal and propanal are carried out, forming a reaction mixture comprising dimer and trimer aldehydes, the reaction mixture is separated, trimer aldehydes being passed to a hydrogenation zone to form either saturated aldehyde or saturated alcohol as desired, the dimer aldehydes being returned to the multipurpose reaction zone.

In all three embodiments, aldolization catalyst, advantageously in the form of an aqueous solution, is fed into at least the first zone in which aldolization is carried out; since aldolization produces water, the catalyst and the product water are advantageously separated and the catalyst returned to the aldolization zone. Advantageously, in the first embodiment, catalyst solution is also fed to the second aldolization zone.

In a fourth embodiment, a multi-purpose reaction zone is provided in which zone dimerization of propanal and reaction of propanal with 2-methylpentanal are carried out and, within the reaction zone, the dimer and trimer components are separated by distillation, the unsaturated dimer being passed to a first hydrogenation zone, selectively hydrogenated to 2-methylpentanal, and returned to the multi-purpose zone, the $C_9$-comprising component being hydrogenated in a second hydrogenation zone to the saturated aldehyde or alcohol as desired. Advantageously in this embodiment, at least some of the water resulting from the aldolizations is removed as vapour with the dimer, condensed, and separated therefrom.

In any aldolization zone containing two or more different aldehydes, a number of different reactions may take place. In general, a smaller aldehyde is more reactive in the conditions advantageously used in the present process than a larger, in part because of its higher solubility in the aqueous catalyst-containing phase; further a linear or a less-branched aldehyde is more reactive than a branched or more branched aldehyde (an α-branched aldehyde being specifically less reactive and incapable of self-aldolization); accordingly where, as in the present invention, it is desired to achieve "cross-aldolization" of $C_6$ and $C_3$ aldehydes, it is desirable, in the second aldolization zone in the first embodiment described above, to minimize condensation of two $C_3$ molecules. To this end, the saturated $C_6$ aldehyde is advantageously maintained in stoichiometric excess relative to the $C_3$ aldehyde, and preferably in a molar ratio of at least 1.5:1. Also, advantageously, the $C_3$ aldehyde is reacted almost completely in the second zone. In the second embodiment, the stoichiometric ratio of $C_6$ to $C_3$ aldehyde is desirably maintained so as to form unsaturated $C_6$ aldehyde at the same rate as saturated $C_6$ aldehyde is consumed by the cross-aldolization reaction.

The stereoisomers produced by the process of the invention may if desired be separated by the procedures known in the art and the invention also provides the products in their enantiomeric forms.

The $C_9$ acids produced by the process of the invention have utility in the manufacture of alkyd resins, synthetic lubricants and refrigerant oils. The esters of the $C_9$ acids with monohydric alcohols, especially alkanols, having at least 6 carbon atoms, especially from 6 to 24, and more especially from 6 to 12, carbon atoms, have especial utility as lubricants and lubricant components. Also especially useful in this field are the esters of the $C_9$ acids with polyhydric alcohols, i.e., those containing at least two hydroxy groups, for example, pentaerythritol, di(pentaerythritol), tri(pentaerythritol); trimethylolethane, trimethylolpropane, trimethylolbutane, and dimers and trimers thereof; and neopentylglycol.

The invention accordingly also provides an ester of a monohydric alcohol having at least 6 carbon atoms, especially from 6 to 24, more especially from 6 to 12, carbon atoms, and 2,4-dimethylheptanoic acid. The invention further provides an ester of a polyhydric alcohol and 2,4-dimethylheptanoic acid other than a tetraester of pentaerythritol, 2-methylhexanoic acid and 2,4-dimethylheptanoic acid, and a refrigerant fluid containing such an ester of the acid with a polyhydric alcohol.

The acid derivatives, especially their esters, have especial utility in providing components for biodegradable lubricant systems. Oxidatively stable lubricants may be made by partial esterification of a polyol with the $C_9$ acid, i.e., esterification leaving an unreacted hydroxy group in the molecule. The metal salts of the acid have utility as catalysts, paint dryers, and pvc stabilizers, while the peroxy esters of the acid are useful as polymerization initiators.

The $C_9$ aldehydes are valuable intermediates, especially in the manufacture of $C_9$ amines, ether amines, and components for the fragrance industry, for example, through condensation with benzaldehyde.

As indicated above, the saturated $C_9$ and other alcohols produced by the process of the invention, primarily 2,4-dimethylheptanol, themselves have utility as processing aids in the thermoplastics and textile industries and as solvents for coatings and paints. They are useful as intermediates in the manufacture of ethers, for example, ethoxylate and other detergent bases. They are especially valuable as intermediates in the manufacture of esters suitable for use as solvents, paint coalescers, plasticizers, adhesives, viscosity index improvers, synthetic lubricants, lubricant components, hydraulic fluids, cetane improvers, drilling fluids, thermoplastic and textile processing aids, polymerizable monomers (e.g., with acrylic and methacrylic acids) and fragrances, by reaction with appropriate acids, for example, by reaction with monobasic or polybasic, e.g., tribasic or more especially dibasic acids, or where appropriate derivative of the acids, e.g., anhydrides, or by transesterification with other, e.g., methyl, esters.

The acid may be inorganic or organic; if the latter, carboxylic acids are preferred. Among organic acids, aromatic acids are preferred for plasticizer manufacture, although aliphatic acids are also employed. As examples of acids, acetic, and its homologues, e.g., propionic, acids, acrylic, neodecanoic, lauric, stearic, iso-stearic, erucic, phthalic (1,2-benzenedicarboxylic), isophthalic, terephthalic, adipic, fumaric, azelaic, sebacic, trimellitic, pyromellitic, tall oil, napthenic and napthalene-type acids, carbonic, phosphoric and phosphorous, acids and $C_6$ to $C_{13}$ oxo and neo acids generally may be mentioned. Esters with monobasic and dibasic acids are preferred for lubricants and lubricant components; advantageously the resulting esters contain from 15 to 40 carbon atoms; adipates and phthalates are especially preferred for lubricant manufacture.

The invention accordingly also provides an ester of 2,4-dimethylheptanol, especially an ester of the alcohol with a polybasic acid, especially an ester with a dibasic acid, other than 2,4-dimethylheptyl 4,6-dimethylheptyl phthalate. The invention also provides an ester of a polybasic acid in which all the acid groups are esterified by 2,4-dime thylheptanol, especially a dibasic acid both acid groups of which are thereby esterified. Among specific esters provided by the invention there may be mentioned, for example, 2,4-dimethylheptyl acetate, the bis(2,4-dimethylheptyl) esters of 1,2-benzenedicarboxylic and hexanedioic acids and the tris ester of 1,2,4-benzenetricarboxylic acid, the latter providing a plasticized polymer with good electrical properties. In vinyl chloride polymer compositions, the plasticizer, especially phthalate, ester, acts as a softening aid for the polymer, a plasticized polymer (e.g. pvc) of a given hardness containing less polymer than comparable plasticized materials, prepared with other $C_9$ phthalate esters, thereby giving the esters of the invention an economic advantage as a result of the resulting volume cost advantage. The phthalate ester also has advantages in the manufacture of automotive sealant compositions in part because of their increased viscosity and enhanced viscosity stability of the composition. Its oxidative stability, stain resistance and foaming properties are comparable with those of Jayflex DINP.

The acetic acid ester has a characteristic floral odour, and may be used as a fragrance.

The invention also provides a plasticizer composition comprising the ester of a polybasic acid and an alkanol blend comprising a major proportion of 2,4-dimethylheptanol and a minor proportion (up to 50%) of another alkanol or alkanols having from 6 to 12 carbon atoms, the alkanols having 6 to 12 carbon atoms including, for example, 2-methylpentanol and 2,4,6-trimethylnonanol. The other alkanols may be linear or branched, or mixtures thereof.

If an aldehyde other than propanal is also present in the aldol reaction mixture, then a mixture of aldol products will be formed having a range of carbon atom numbers, as a result of cross-aldolization. The invention accordingly also provides the esters obtained by reaction of the resulting alcohol mixture with an acid. It will be appreciated that, where the acid is polybasic, mixed esters will be present.

If desired, however, this mixture may be separated into different fractions, which may then be used as intermediates for various derivatives. For example, if 2-methylpropanal is present with the starting propanal, it will perforce condense with propanal only, giving first 2,4-dimethyl-2-pentenal, after hydrogenation 2,4-dimethyl-pentanal, after another aldol step 2,4,6-trimethyl-2-heptenal, and after hydrogenation 2,4,6-trimethyl-heptanal, which may give either by oxidation 2,4,6-trimethyl-heptanoic acid or by hydrogenation 2,4,6-trimethyl-heptanol. Both the acid and the alcohol may offer specific advantages in the usual derivatives, for example, the polyol esters or plasticizer esters, which are also accordingly provided by the invention. In other embodiments, n-butanal or a mixture of n-butanal and isobutanal may be present in admixture with the propanal.

More especially, the ester may be the reaction product of an acid, especially a polybasic acid, and a blend of alkanols comprising a major proportion of 2,4-dimethylheptanol and a minor proportion (up to 50%), especially up to 25%, of $C_{10}$ alkanols.

The invention further provides a composition comprising a plasticizer ester, or plasticizer composition, according to the invention and a polymer plasticized thereby. The invention also provides a shaped structure formed of the plasticized polymer. Advantageously, the ester is made by a process in accordance with the invention.

The esters may be produced by methods known per se or described in the literature from the alcohol and the relevant acid or, preferably, where appropriate, the anhydride, optionally in the presence of a solvent. Elevated temperatures and reduced pressures are generally employed to drive the reaction toward completion by removal of the water produced. Catalysts may be employed. Suitable catalysts include, for example, a titanium catalyst e.g., a tetraalkyl-titanate, especially tetra-iso-propyl or tetraoctyl ortho titanate, or a sulphonic acid, e.g., p-toluene sulphonic acid or methylsulphonic acid. Any catalyst present in the reaction product may be removed by alkali treatment and water washing. Advantageously, the alcohol is used in slight, e.g., from 10 to 25%, molar excess relative to the number of acid groups in the acid.

The esters of the invention may be used as a plasticizer for numerous polymers, for example, cellulose acetate; homo- and copolymers of aromatic vinyl compounds e.g., styrene, or of vinyl esters with carboxylic acids e.g., ethylene/vinyl acetate copolymers; halogen-containing polymers, especially vinyl chloride homo- and copolymers, more especially those copolymers with vinyl esters of carboxylic acids, esters of unsaturated car-boxylic acids e.g., methacrylates, and/or olefins; nitrile rubbers; and post-chlorinated vinyl chloride polymers. Poly(vinyl chloride) is of especial interest.

The proportion of plasticizer may vary within wide limits, but is generally 10 to 200 parts by weight per 100 parts of polymer, more especially 20 to 100 parts per 100.

The esters of the invention may be used alone as plasticizer, or in admixture with other plasticizers, for example, dibutyl, dipentyl, dihexyl, diheptyl, dioctyl, dinonyl, didecyl, diundecyl, didodecyl, ditridecyl phthalates, trimellitates or adipates, or butyl benzyl phthalate, or mixtures thereof. They may also or instead be used with a secondary plasticizer, e.g., a chlorinated paraffin, Texanol isobutyrate, or a processing oil. If used in admixture, it is the total proportion of plasticizer that is advantageously within the ranges given above.

The plasticized polymeric compositions of the invention may be made up in numerous forms and have various end-uses. For example, they may be in the form of a dryblend, a paste, or a plastisol, depending on the grade of the resin employed. They may be used, for example, as coatings, in dipping, spraying, injection or rotational molding, extrusion, or as self-supporting films and sheets, and may readily be foamed. End uses include flooring materials, wall coverings, molded products, upholstery materials, leather substitutes, electrical insulation, especially wire and cable, coated fabrics, toys, and automobile parts.

The properties of the polymers plasticized by 2,4-dimethylheptanol esters are comparable to those using presently available plasticizer esters of $C_8$ and $C_9$ alkanols. As compared to diethylhexyl phthalate, the plasticizer volatility is lower, other properties being broadly comparable, while in comparison to a diisononyl phthalate, in which the alcohol is derived from a butene dimer olefin, plastisol viscosity stability is enhanced and, as indicated above, there is the advantage of a single isomer product.

Various embodiments of the process of the invention will now be described in greater detail by way of example only with reference to the accompanying drawings, in which:

BRIEF DESCRIPTION OF THE DRAWINGS

Each of FIGS. 1 to 6 is a schematic flow diagram of a process for the manufacture of a $C_9$ alcohol from a $C_3$ aldehyde, FIGS. 1 and 2 being embodiments employing two aldol reactors and a separate intermediate hydrogenation reactor.

Figure 1:
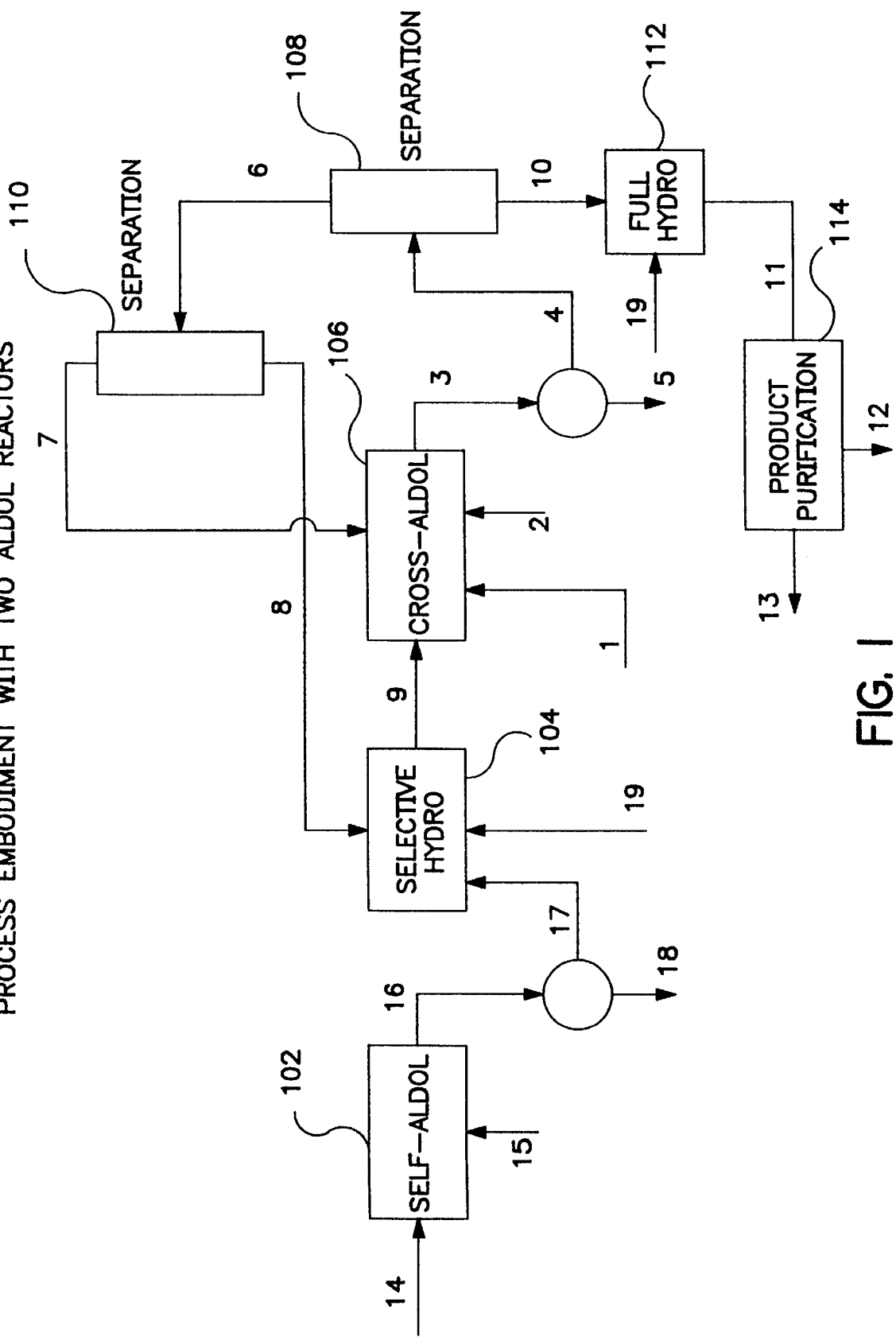

In each Figure, reference numerals below 100 refer to feed and product streams.

Referring now to FIG. 1, aldehyde monomer 14 and catalyst solution 15 are fed to a self-aldol reactor 102, where dimerization occurs to make the α,β-unsaturated dimer aldehyde and water 16. The water phase 18 is removed, and the organic phase 17 is sent to a selective hydrogenation reactor 104 together with hydrogen 19. In the selective hydrogenation reactor 104, the α,β-unsaturated dimer aldehyde is converted to the saturated dimer aldehyde 9. Saturated dimer aldehyde then enters a cross-aldol reactor 106, where it is cross-condensed with additional aldehyde monomer 1 in the presence of a catalyst solution 2. In the cross-aldol reactor, the saturated dimer aldehyde is advantageously present in stoichiometric excess relative to-the monomer aldehyde. This enhances selectivity of trimer production and suppresses monomer self-condensation in the cross-aldol reactor. Monomer aldehyde is advantageously reacted to almost complete conversion in the cross-aldol reactor. Water 5 is removed from the cross-aldol product 3, and the organic phase 4 is sent to a separator 108. In the separator, trimer aldehydes and heavy by-products 10 are removed as bottoms and dimer aldehydes and light components are taken overhead 6. The dimer aldehydes are optionally further separated in a separator 110 into saturated dimer aldehyde 7 and unsaturated dimer aldehyde 8. The saturated dimer aldehyde 7 is recycled to the cross-aldol reactor 106, and the unsaturated dimer aldehyde 8 is recycled to the selective hydrogenation reactor 104. If the separator 110 is omitted, the stream 6 may all be fed to the selective hydrogenation reactor 104 or it may be divided with part being fed to the reactor 104 and part to the cross-aldol reactor 106. This applies, mutatis mutandis, to all embodiments, as does the possibility of separating the aqueous phase 5 from the organic phase after taking the trimer from the separator 108. A small purge stream may be removed from stream 6 or 7 to prevent the build-up of light by-products in the recycle loop.

Trimer aldehyde products 10 are hydrogenated, optionally after further distillation in a column (not shown) to remove heavies, by hydrogen 19 in a hydrogenation reactor 112 to make saturated alcohols 11. By-products 12 are removed in a product purification section 114 to yield high-purity higher alcohols 13.

Water from the process 5,18 is sent to a catalyst recovery section (not shown) where the aqueous stream is concentrated back to its original strength and returned to the process as catalyst streams 2,15.

Figure 2:
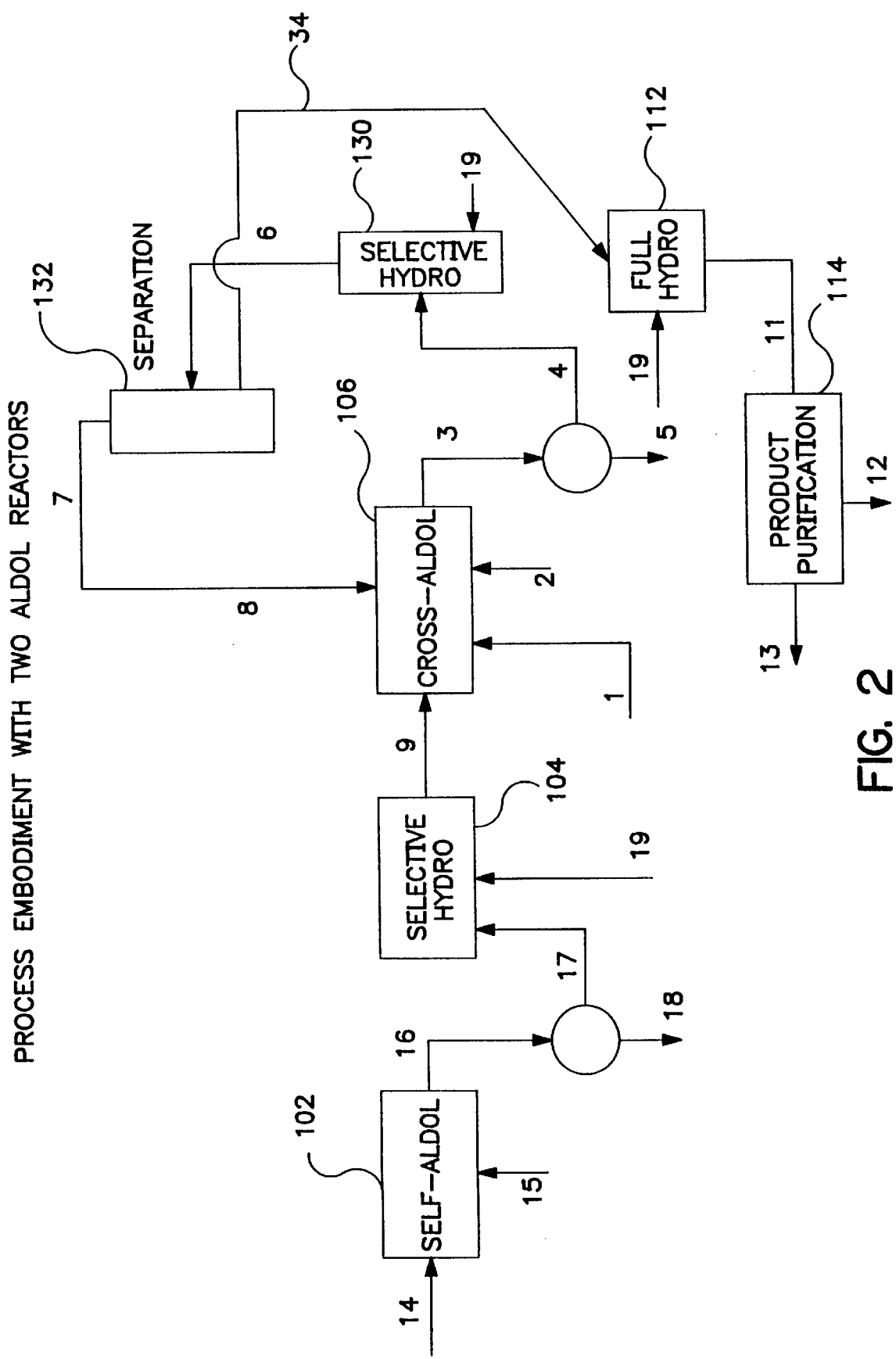

Referring to FIG. 2, which shows a variation of the embodiment illustrated in FIG. 1, the organic phase 4 of the product from the cross-aldol reactor 106 is passed to a hydrogenation reactor 130 where selective hydrogenation to saturated dimer and trimer aldehydes is effected. The product is passed to a separator 132, whence the dimer aldehyde 7 is returned to the cross-aldol reactor 106 and the trimer aldehyde 34 is passed to the hydrogenation reactor 112 to make saturated alcohol 11.

Figure 3:
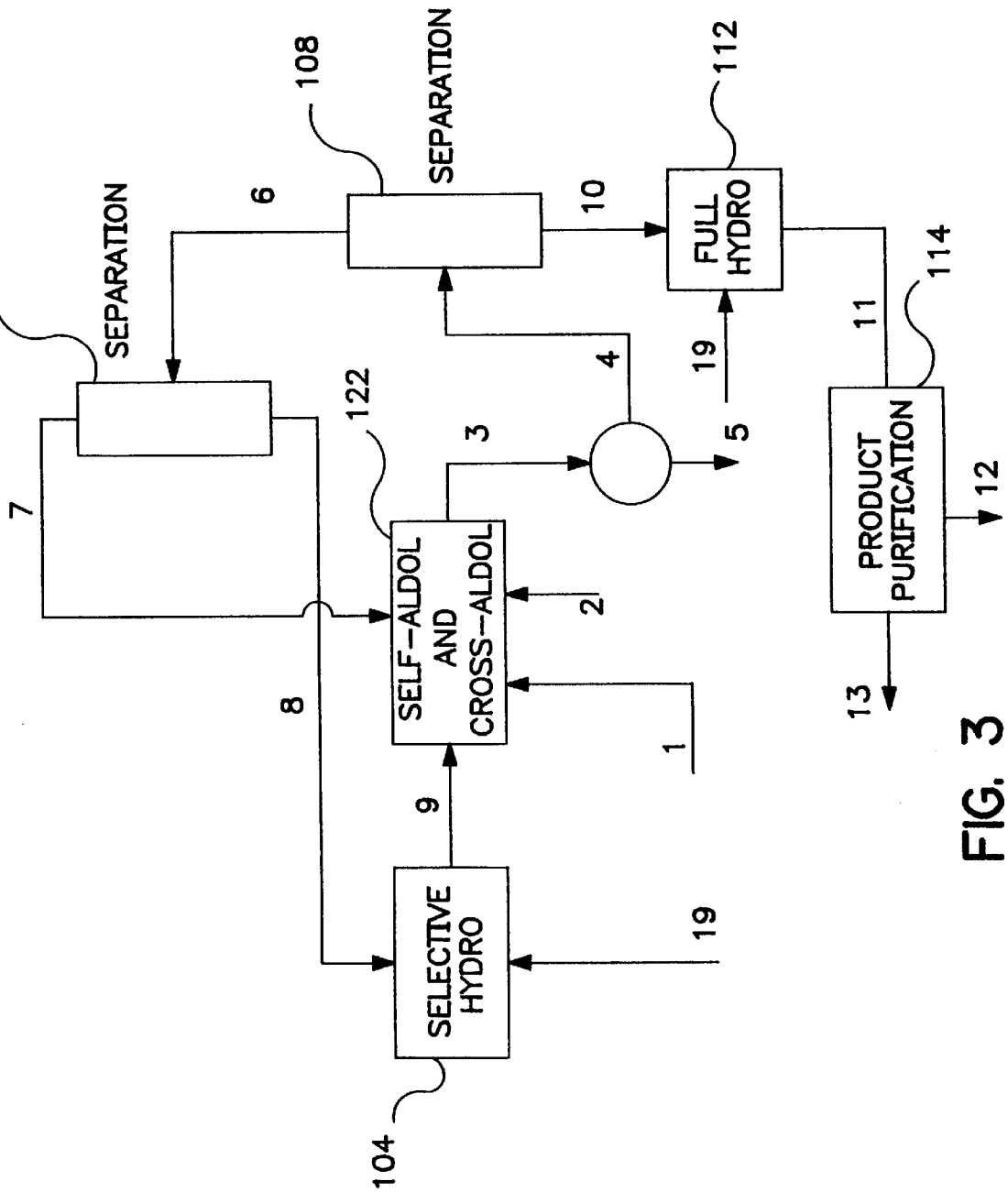
FIGS. 3 and 4 being embodiments employing a single aldol reactor and a separate hydrogenation reactor.

In the embodiment of FIG. 3, only one aldol reactor 122 is used. All of the monomer aldehyde 1 is fed to the aldol reactor 122 with the saturated dimer aldehyde 7,9 and catalyst solution 2. In this aldol reactor 122, the monomer aldehyde both self-condenses to make unsaturated dimer and cross-condenses with saturated dimer aldehyde to make unsaturated trimer. The stoichiometric ratio of dimer to monomer aldehyde is advantageously controlled to optimize selectivity to the desired product. Water removal 5, product separation and recycle 108, 110, hydrogenation 112 and product purification 114 are all identical to the corresponding steps in FIG. 1.

Figure 4:
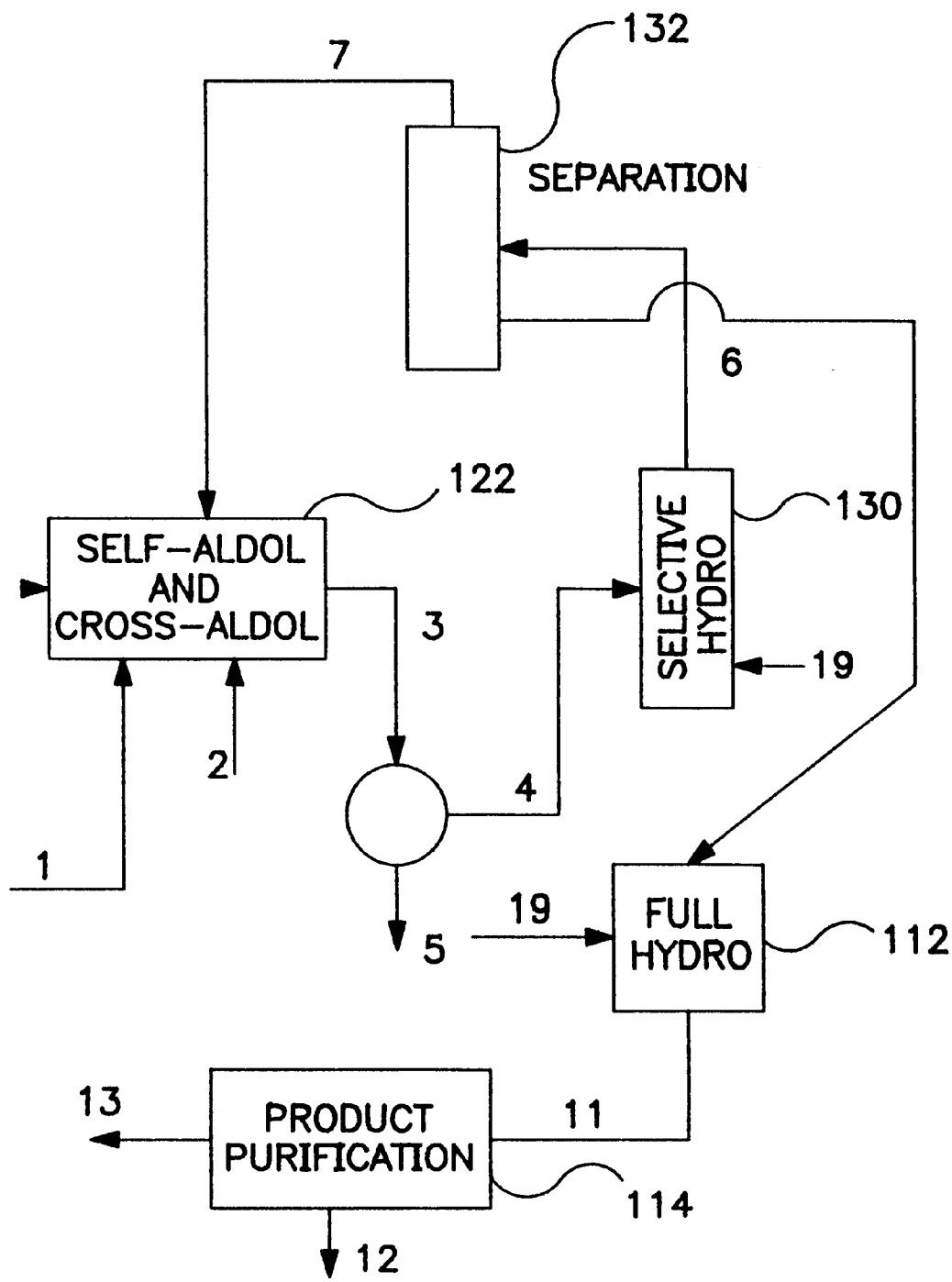

Referring now to FIG. 4, which shows a variation of the embodiment illustrated in FIG. 3, the organic phase 4 of the product from the single aldol reactor 122 is passed to a hydrogenation reactor 130 where selective hydrogenation to saturated dimer and trimer aldehydes is effected. The product is passed to a separator 132 whence dimer aldehyde 7 is returned to the aldol reactor 122 and the trimer aldehyde passed to the hydrogenation reactor 112 to make saturated alcohol 11.

In the embodiments of each of FIGS. 1 to 3, the separation of saturated and unsaturated dimer aldehydes in stream 6, or stream 7 in FIG. 2, is optional. If the selective hydrogenation does not convert a large proportion of saturated dimer aldehyde to alcohol, then stream 6 or 7 may be recycled directly back to the selective hydrogenation reactor 104 without yield loss to the overall process. The saturated dimer aldehyde would pass through the selective hydrogenation as an inert diluent and this could be advantageous as a means of controlling the temperature of the selective hydrogenation.

Figure 5:
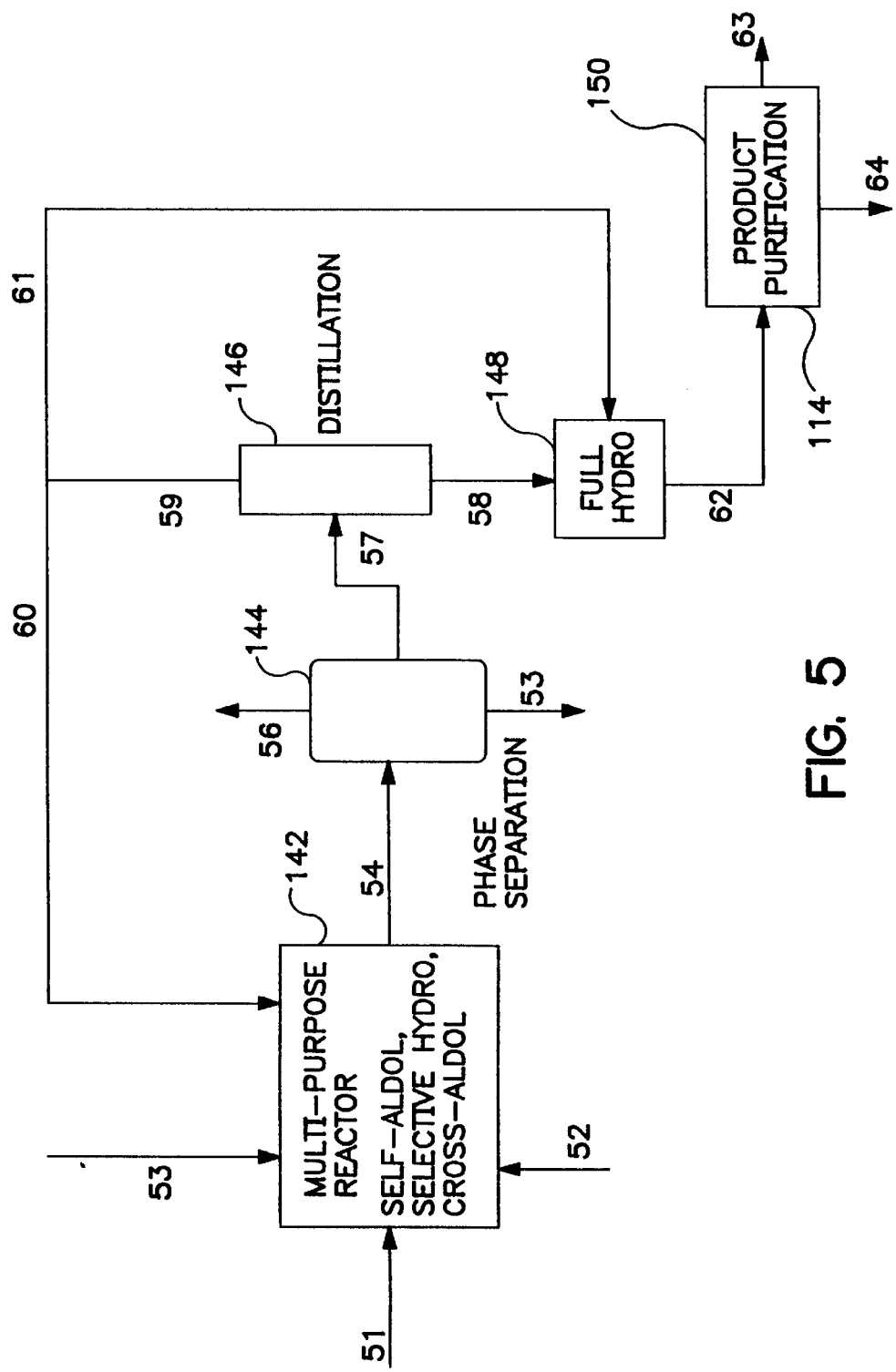
FIG. 5 being an embodiment in which a single reactor is used for hydrogenation and aldolization, FIG. 6 being an embodiment in which a single reactor is used for aldolization and aldol product separation.

In the embodiment shown in FIG. 5, aldehyde monomer 51, aqueous catalyst solution 52, and hydrogen 53 are fed to a multi-purpose reactor 142. The reactor 142 also contains a heterogeneous hydrogenation catalyst, such as palladium supported on carbon. In this reactor 142, three major reactions proceed simultaneously; they are: self-condensation of monomer aldehyde to make α,β-unsaturated dimer aldehyde, selective hydrogenation of the α,β-unsaturated dimer aldehyde to make saturated dimer aldehyde, and cross-condensation of monomer with saturated dimer to make α,β-unsaturated trimer aldehyde. The effluent 54 from this reactor 142, consisting of saturated and unsaturated dimer and trimer aldehydes, is sent to a phase separator 144 where the aqueous catalyst 55 and unreacted hydrogen 56 are removed. The organic effluent 57 is sent to a distillation column 146 which splits trimer aldehydes and heavier components in the bottoms 58 and dimer aldehydes and lighter components in the overhead 59. The overhead stream 60 is recycled to the multipurpose reactor 142. A purge 61 may be taken from the recycle stream to prevent the buildup of unwanted light components. The distillation bottoms, optionally distilled further to reduce heavies, and if desired the purge stream are sent to a full hydrogenation reactor 148 where unsaturated and saturated aldehydes are fully hydrogenated to saturated alcohols 62. The alcohol stream is then purified in a purification section 150 as required by downstream usage, desired product being taken off in stream 63, impurities being removed in stream 64.

Hydrogenation of carbon-carbon double bonds, but not carbon-oxygen double bonds, is favoured in the reactor 142. Therefore, some of the unsaturated trimer aldehyde is hydrogenated to form saturated trimer aldehyde, which is present in the effluent of the reactor 142. This saturated trimer aldehyde yields the saturated alcohol product upon full hydrogenation in the reactor 148.

If hydrogenation conditions are extreme (high temperature and hydrogen partial pressure) in the reactor 142, then carbon-oxygen double bonds may be hydrogenated in addition to carbon-carbon double bonds, leading to the production of saturated dimer and trimer alcohols in the first reactor. This is undesirable for maximum trimer selectivity. However, if dimer alcohols or other intermediates are also wanted, then this is not detrimental and may even be desired.

Figure 6:
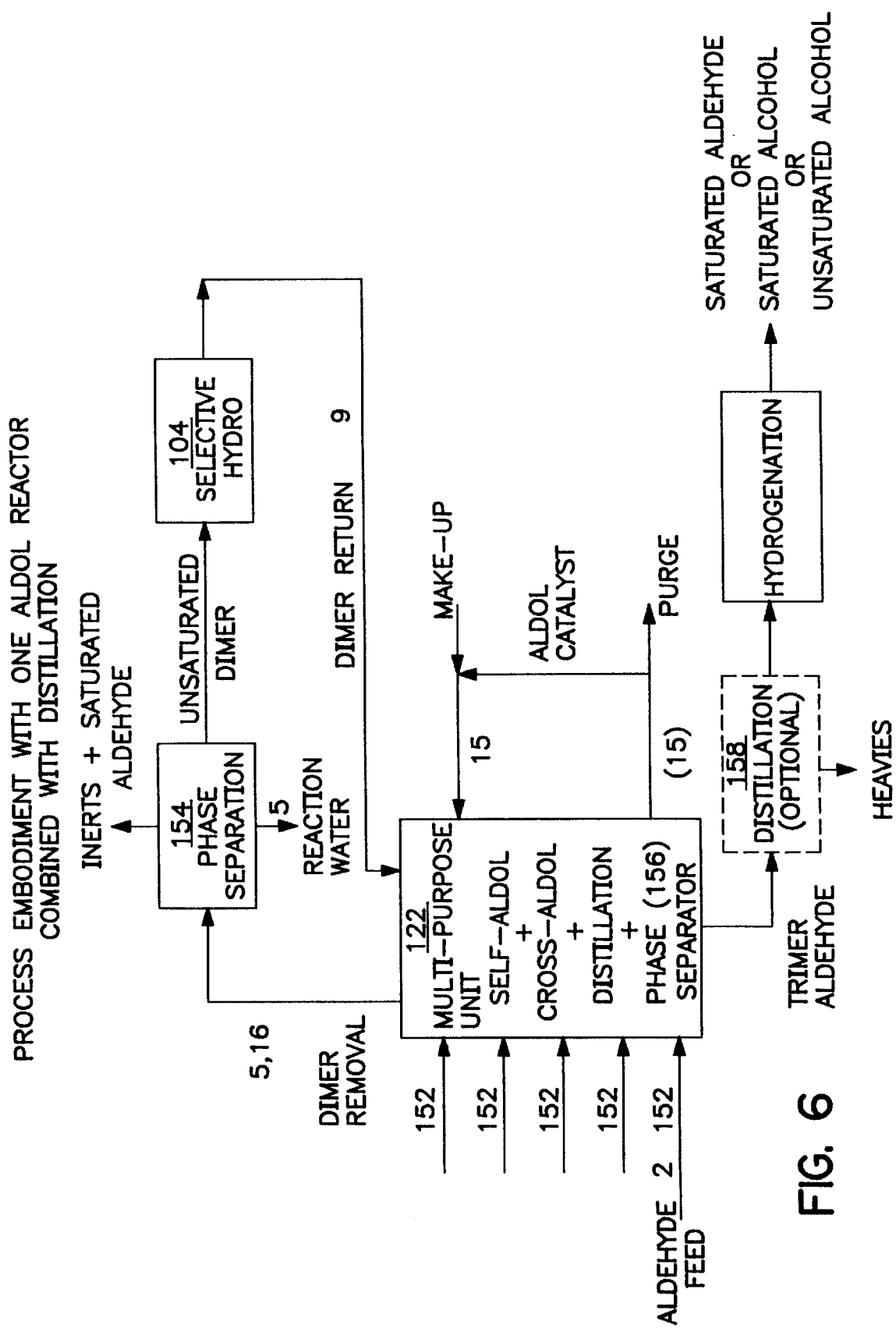

In the embodiment of FIG. 6, like that of FIG. 3, only one aldol reactor 122 is used, but in this embodiment the reactor 122 is in the form of a distillation column in which various separations are effected. The monomer aldehyde 1 catalyst solution 15, and saturated dimer aldehyde 9 are fed to the column, the ratio of dimer to monomer aldehydes being controlled by metering the monomer aldehyde feed through valves 152. The water, stream 5, resulting from aldolization is taken off overhead with the unsaturated dimer aldehyde 16, and separated from the aldehyde in a separator 154. The unsaturated dimer aldehyde is hydrogenated to saturated aldehyde in a selective hydrogenation reactor 104 and returned to the reactor 122.

Trimer aldehyde and catalyst solution 15 are taken from the reactor 122 as bottoms and separated in a separator 156, the catalyst solution 15 being returned to the reactor 122 while the trimer aldehyde, after being separated from heavies in a column 158, is passed to full hydrogenation and further treatment as shown in previous figures.

Figure 7:
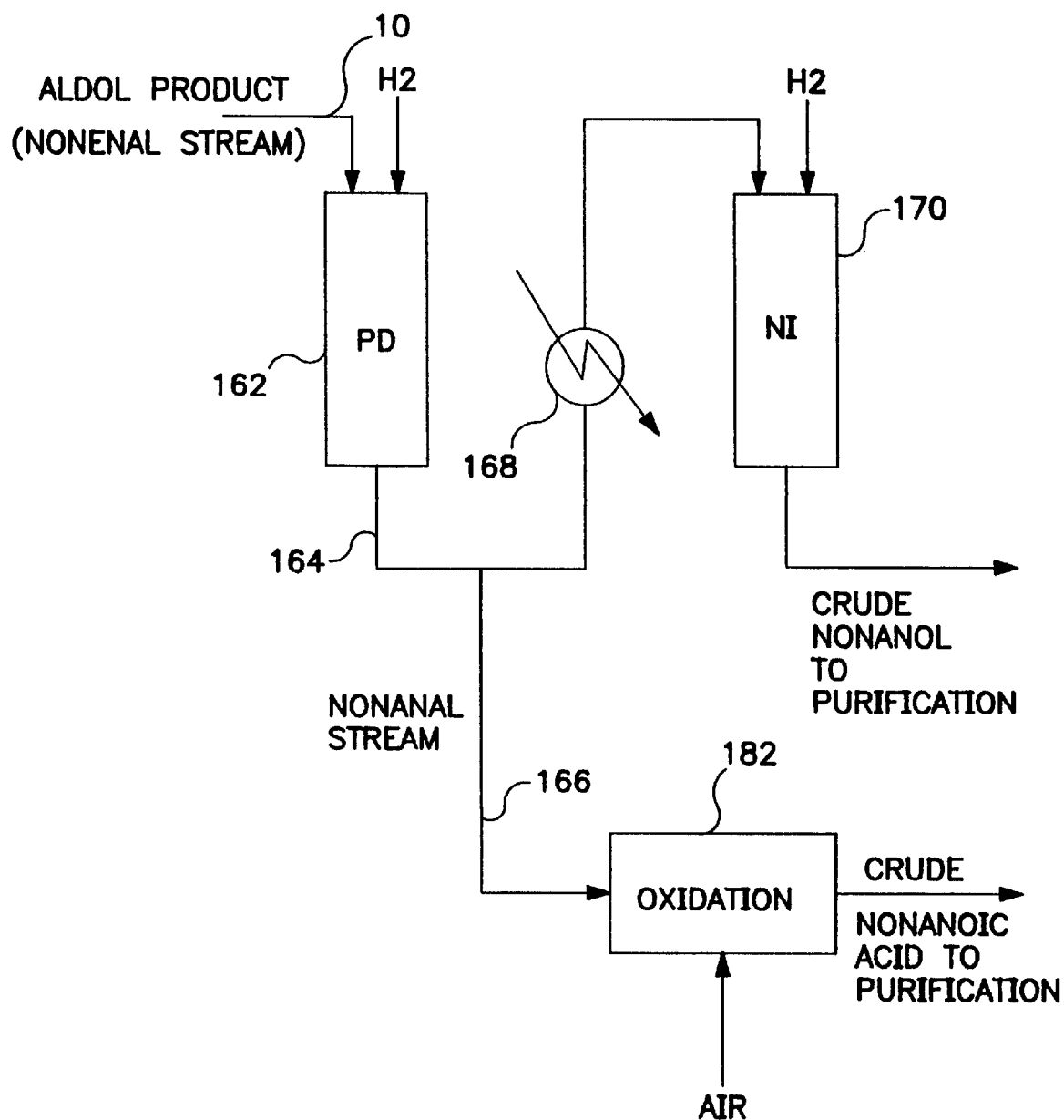
FIG. 7 illustrates an embodiment with a modified hydrogenation procedure.

Referring now to FIG. 7, there is shown an alternative to the single hydrogenation reactor 112 or 148 shown in FIGS. 1 to 5. In FIG. 7, the nonenal stream 10 is fed first to a selective hydrogenation reactor 162, whence a saturated aldehyde stream is fed by a line 164, from which a branch 166 is taken, which will be referred to below. After cooling in a heat exchanger 168, the saturated aldehyde stream is fed to a further hydrogenation reactor 170, to form a saturated alcohol.

If desired, some or all of the saturated aldehyde in the line 164 is taken through the line 166 to an oxidation reactor where $C_9$ acid is produced.

In general, the unsaturated dimer aldehyde referred to above will be 2-methyl-2-pentenal; the saturated dimer aldehyde will be 2-methylpentanal; the doubly and singly unsaturated, and saturated, trimer aldehydes will be 2,4-dimethyl-2,4-heptadienal, 2,4-dimethyl-2-heptenal, and 2,4-dimethylheptanal respectively, and the saturated alcohol will be 2,4-dimethylheptanol, but other isomers may be formed.

The following Examples, in which parts and percentages are by weight unless otherwise stated, illustrate the invention.

Part A—Hydroformylation

EXAMPLE 1

Rhodium was charged to a reactor, a 300 ml stainless steel autoclave, equipped with stirrer and temperature control unit, in the form of a solution of $HRh(CO)(PPh_3)_3$, or of $Rh(CO)_2(acac)$, where $PPh_3$ is triphenylphosphine, in toluene. $Rh(CO)_2(acac)$ was purchased from Strem Chemicals and was used as received. $HRh(CO)(PPh_3)_3$ was prepared from $Rh(CO)_2(acac)$ by the method described in Inorg. Synth. 1974,15, 59. The solution was charged under flow of nitrogen into the autoclave. The unit was then flushed with syngas ($H_2/CO=1$). When the catalyst was prepared in situ the autoclave was pressurized to about 0.5 MPa at room temperature, then heated up to 100° C., and was kept at that temperature for about 30 minutes. Independent experiments demonstrated that under these conditions the rhodium loses the acac ligand by hydrogenation and the formed hydridocarbonyl triphenylphosphino rhodium complex (es) $(HRh(CO)_x(PPh_3)_y, x+y=4)$ catalyse hydroformylation without showing any induction period. When $HRh(CO)(PPh_3)_3$ was used as a Rh source no catalyst preforming was necessary.

Where required, the autoclave was connected to a 500 ml high pressure buffer bomb through a regulator valve.

The reactor containing the solution of preformed catalyst was flushed and pressurized with Gas Mixture No.1 containing ethylene, ethane, acetylene, carbon dioxide, hydrogen, methane, carbon monoxide, and nitrogen, in the proportions given in Table 1, at room temperature. The quantity of gas loaded into the reactor was determined by the gas volumetric method. The P/Rh ratio in this example was 300, and the reaction temperature 100° C. The composition of the catalyst charged is given in the footnote to Table 1. After heating the reaction mixture to 100° C., a fast pressure drop in the autoclave was observed indicating that a gas consuming reaction took place. This pressure drop significantly slowed down after about 45 minutes when the reaction was stopped by cooling the reaction mixture to 15° C. After cooling the system below room temperature gas and liquid samples were taken, and analysed by GC. The results are given in Table 2.

TABLE 1

Hydroformylation of Multi-component Syngas (Gas Mixture No. 1) at 100° C.

| Compound | $x°$ (v %) | $n°$ (mmol) | $n^f$ (mmol) | dn (mmol) |
|---|---|---|---|---|
| $C_2H_4$ | 9.91 | 9.49 | 0.77 | −8.72 |
| $C_2H_6$ | 3.26 | 3.12 | 1.69 | −1.43 |
| $C_2H_2$ | 6.83 | 6.54 | 1.08 | −5.46 |
| $CO_2$ | 2.53 | 2.42 | 1.51 | −0.91 |
| $H_2$ | 48.27 | 53.09 | 47.17 | −5.92 |
| $CH_4$ | 11.70 | 11.21 | 9.14 | −2.07 |
| CO | 17.50 | 23.32 | 8.65 | −14.67 |
| Propanal* | — | — | 14.20 | +14.20 |
| Total | 100.00 | 109.19 | 84.21 | −24.98 |

Reaction conditions: toluene: 60 ml, methyl cyclohexane (internal standard for GC): 0.8 ml, Rh: 64.3 μmoles, $PPh_3$: 19.3 mmoles, p° = 800 kPa (at 100° C.), reaction time at 100° C.: 45 min.
Legand: $x°$ = initial gas concentration, $n°$ = initial number of mmoles in the gas phase, $n^f$ = final number of mmoles in the gas phase, dn = mole number change in the gas phase.
*Liquid GC result.

The solution sample taken at the end of the experiment was bright orange yellow, indicative of an active catalyst system in the conversion of acetylene-and ethylene-containing multi-component syngas mixtures.

EXAMPLE 2 to 8

These examples illustrate the effect of varying the Rh:$PPh_3$ ratio.

The preparation and loading procedure of the catalyst solutions were the same as in Example 1. The solvent, tetraethylene glycol dimethyl ether (tetraglyme), which also served as an internal standard in the GC analyses of the liquid product samples, was deaerated before use. The solution volume and the total initial gas charge in each example were the same, 70 ml, and 95 mmoles, respectively. The apparatus was the same as in Example 1 except that a feed line from a volume calibrated high pressure injection bomb was mounted in the feed line between the pressure regulator valve and the autoclave. This injection bomb was used to inject known amounts of ethylene/acetylene mixtures into the autoclave. The ethylene and acetylene charges in each example were about 15.4 and 6.4 mmoles, respectively. Batch kinetic experiments were carried out at constant 1 MPa total gauge pressure and 120° C. As the reaction proceeded a constant pressure was maintained by feeding syngas ($CO/H_2$=1) from the high pressure bomb through the regulator valve. The reaction was monitored by reading the pressures in the bomb as a function of time. The overall conversions of ethylene and acetylene were determined after each run by GC analyses of the liquid and gas products. The only two products of the reactions detected were propanal as major product and a minor amount of ethane. The overall conversion was then correlated to the total pressure drop and the total gas consumption in the bomb during the experiment. Reaction rates were calculated assuming a linear correlation between the pressure drops and $C_2$ unsaturates conversions. The catalyst compositions and results of the six examples are shown in Table 2.

TABLE 2

| Example | $PPh_3$ (mmoles) | Rh (μmoles) | P/Rh | Initial Rate (mol/mol Rh/sec) | Total $C_2$ Conversion (%) |
|---------|------------------|-------------|------|-------------------------------|----------------------------|
| 2       | 1.17             | 37.7        | 31   | 0.04                          | 80                         |
| 3       | 4.32             | 37.7        | 115  | 0.1                           | 80                         |
| 4       | 8.45             | 37.4        | 226  | 0.3                           | 80                         |
| 5       | 16.37            | 37.6        | 435  | 0.9                           | 92                         |
| 6       | 23.40            | 38.0        | 660  | 2.1                           | 99                         |
| 7       | 30.93            | 18.8        | 1644 | 2.1                           | 99                         |

Kinetic data in Table 2 demonstrate that the activity of the catalyst increases significantly with an increase in phosphine concentration. The final solutions were orange yellow.

Part B—Aldol Condensation & Hydrogenation

EXAMPLE 8 and 9

Examples 8 and 9 demonstrate the self condensation of propanal, the first step of the aldol process. Example 9 shows that heavies formation is reduced when an inert solvent is present in the reaction mixture.

EXAMPLE 8

Self Condensation of Propanal

Into a 300 ml autoclave were added 66g of a molar sodium hydroxide solution. The catalyst solution was heated to 100° C., then 110.83 g (1.908 mole) propanal and 2.61 g (0.0183 mole) decane (internal standard) were added in 14 minutes with 1295 rpm stirring and at 0.76 MPa to 1.86 MPa pressure. The reaction mixture was sampled for GC analysis after complete addition. The reaction mixture contained: propanal (0.29%). 2-methyl-2-pentenal (86.44%), decane (2.80%), 2,4-dimethyl-2-heptenal (0.17%), 2,4-dimethyl-2,4-heptadienal (1.90%) and heavies (8.40%).

EXAMPLE 9

Self Condensation in Presence of Hydrocarbon Solvent

Into a 300 ml autoclave were added 50 g of a molar sodium hydroxide solution and 77.86 g (0.925 mole) cyclohexane. The two phased mixture was heated to 95° C. in 20 minutes. At 95° C., 41.67 g (0.7174 mole) propanal and 0.9813 g (0.0069 mole) decane (internal standard) were added all at once to the stirred cyclohexane/aqueous sodium hydroxide solution. The reaction mixture cooled to 79° C. on addition, returning to 97° C. in one minute. The reaction mixture was then sampled for GC analysis. The reaction mixture contained: propanal (0.40%), cyclohexane (68.19%), 2-methyl-2-pentenal (29.33%), decane (0.86%), 2,4-dimethyl-2,4-heptadienal (0.08%) and heavies (1.14%).

EXAMPLE 10

Continuous Production of 2-methylpentanal from Propanal (a) Aldolization reaction: a tubular reactor of length 102 m and internal diameter of 1.1 mm was immersed in a thermostatically controlled water bath at 60° C. To the reactor inlet were fed 1050 ml/h propanal and 500 ml/h of an aqueous molar NaOH solution. The reactor design allows short residence times whilst providing a pressure drop facilitating contact between the phases, reducing the heavy by-products make compared. The pressure at the reactor outlet was 1.5 MPa abs. The reactor effluent was decanted to separate the water and organic phases and the organic phase analysed by gas chromatography. The composition was: propanal (0.2 wt %), 2-methylpentenal (89.1 wt %), heavy by-products (10.7 wt % of which about 2 wt % is 2,4-dimethyl-2-heptenal, a precursor of the eventually desired alcohol acid). This corresponds to a conversion of 99.8% and a yield to 2-methylpentenal of 93% of theory.

(b) Aldolization, using sodium carbonate as catalyst: To the inlet of the reactor described in Example 10 (a) were fed 1050 ml/h propanal and 550 ml/h of a 5 weight % sodium carbonate solution. The thermostatic bath temperature was set at 132° C. The pressure at the reactor outlet was 1.5 MPa abs. The reactor effluent was decanted to separate the water phase and the organic phase was analysed by gas chromatography. The composition was: propanal (0.9 wt %), 2-methylpentenal (88.7 wt %), heavy byproducts (10.4 wt %). This corresponds to a conversion of 99.2% and a yield to 2-methylpenenal of 88.8% of theory.

(c) Selective hydrogenation to 2-methyl-pentanal: to a tubular reactor, 1 m long and 1.25 cm diameter, immersed in a thermostatic sandbath, were loaded 130 ml of granules of palladium catalyst supported on carbon (0.5% Pd). To the reactor was fed hydrogen at a rate of 75 1/h. The product of part (a) was pumped to the reactor at a rate of 150 ml/h. The temperature inside the reactor was 102° C., and pressure was 1.5 MPa abs. The reactor feed and product were regularly sampled and analysed by GC. Typical results are given in Table 3.

TABLE 3

| Component, %     | Feed  | Product |
|------------------|-------|---------|
| Propanal         | 0.12  | 0.21    |
| 2-methylpentanal | 0.00  | 84.04   |
| 2-methylpentenal | 86.63 | 0.8     |
| 2-methylpentanol | 0.00  | 0.63    |

TABLE 3-continued

| Component, % | Feed | Product |
|---|---|---|
| Heavy by-products | 13.25 | 14.32 |
| | 100.00 | 100.00 |

This corresponds to a 99.1% conversion of 2-methylpentenal. The selectivity to 2-methylpentanal is 97.9%, with 0.7% selectivity to 2-methylpentanol.

EXAMPLE 11 and 12

These Examples show that selectivity to the desired $C_9$ aldehyde product is greatly enhanced when propanal is cross condensed with 2-methylpentanal rather than with 2-methyl-2-pentenal.

EXAMPLE 11

Cross Condensation of Propanal with 2-methyl-2-pentenal

Into a 300 ml autoclave were added 49.39 g (0.503 mole) 2-methyl-2-pentenal and 41.4 g of molar solution of sodium hydroxide. The mixture was heated to 122° C. in 35 minutes. After reaching this temperature, 7.41 g (0.128 mole) propanal, 0.24 g (0.00169 mole) decane, and 9.83 g (0.117 mole) cyclohexane were added over a period of 20 minutes at 122–125° C., 1225 rpm stirring and 1.2 MPa pressure. The reaction mixture was sampled for GC analysis after complete addition. The reaction mixture contained: propanal (0.67%), cyclohexane (13.32%), 2-methyl-2-pentenal (63.63%), 2-methylpentanal (0.34%), decane (0.33%), 2,4-dimethyl-2-heptenal (0.83%) 2,4-dimethyl-2,4-heptadienal (5.71%), and heavies (15.8%).

EXAMPLE 12

Cross Condensation of Propanal with 2-methylpentanal

Into a 300ml autoclave were added 50 g of a molar solution of sodium hydroxide solution, 69 g (0.69 mole) 2-methylpentanal and 1.41 g (0.0099 mole) decane. The mixture was heated with magnetic stirring (1230 rpm) to 100° C., at which temperature a mixture of 20 g (0.34 mole) propanal, 69 g (0.69 mole) 2-methylpentanal and 1.81 g (0.0127 mole) decane was added over the course of 32 minutes. The pressure was 0.86 MPa at the start of the addition increasing to 2.0 MPa at its completion. The reaction mixture was then sampled for GC analysis. It contained: propanal (0.23%), 2-methyl-2-pentenal (8.57%), 2-methylpentanal (81.91%), decane (1.87%), 2,4-dimethyl-2-heptenal (5.37%), 2,4-dimethyl-2,4-heptadienal (0.05%) and heavies (2.01%).

EXAMPLE 13

In this example, the self condensation and cross condensation are shown to proceed at approximately equal rates. The relative rates are determined by the ratio of propanal and 2-methylpentanal in the feed and by the reaction conditions. Also, since 2-methylpentanal is present in excess, it also plays a role similar to the hydrocarbon solvent in Example 9 and helps to reduce heavies formation relative to Example 8.

Into a 300ml autoclave were added 69.5 g of a molar sodium hydroxide solution. The catalyst solution was heated to 125° C. in 48 minutes with magnetic stirring (1223 rpm) and 1.3 MPa pressure. At 125° C., 13.65 g (0.21 mole) propanal, 96.15 g (0.96 mole) 2-methylpentanal, and 2.19 g (0.0154 mole) decane (internal standard) were added over the course of 12 minutes. The pressure increased to 2.1 MPa during this addition period. The reaction mixture was then sampled for GC analysis and contained: propanal (0.17%), 2-methyl-2-pentenal (6.57%), 2-methylpentanal (81.65%), decane (1.88%), 2,4-dimethyl-2-heptenal (9.31%), and heavies (0.43%).

The net conversion that occurs in this example (excluding the excess 2-methylpentanal) is that 13.5 grams of propanal (monomer) have combined with 8.2 grams of 2-methylpentanal (saturated dimer) to produce 10.0 grams of 2,4-dimethyl-2-heptenal (trimer) and 7.1 grams of 2-methyl-2-pentenal (unsaturated dimer to be hydrogenated and recycled) plus water of condensation.

EXAMPLE 14

Selective Hydrogenation of 2-methyl-2-pentenal to 2-methylpentanal

An autoclave, equipped with a catalyst basket fitting along the autoclave wall, was charged with 161 g of a commercial pelletized palladium catalyst supported on alumina (0.5% Pd). Into the autoclave was added an aldolization product of propanal (crude 2-methyl-2-pentenal) diluted in hexane. The aldolization product was obtained from the reaction of propanal catalysed with 2 M aqueous sodium hydroxide (mass ratio of aqueous to organic phase was 1:4). The organic phase from the reaction product was mixed with n-hexane. The composition of this mixture, as determined by gas-liquid chromatography was: propanal (0.40%), 2-methyl-2-pentenal (13.18%), heavier products (6.42%), and hexane (80%). 1000 g of the mixture were hydrogenated under 1.1 MPa hydrogen pressure at 100° C. The hydrogenation was followed as a function of time by regular sampling and analysis. Table 4 shows the content of 2-methyl-2-pentenal and. 2-methylpentanal as a function of time.

TABLE 4

| Time (minutes) | 2-methyl-2-pentenal (%) | 2-methylpentanal (%) |
|---|---|---|
| 0 (feed) | 13.18 | 0 |
| 60 | 4.27 | 8.94 |
| 90 | 2.20 | 11.14 |
| 150 | 0.46 | 12.63 |

After 150 minutes, the liquid product was drained from the reactor and analysed. The composition was:

propanal (0.05%), 2-methyl-2-pentenal (0.27%), 2-methylpentanal (13.14%), 2-methylpentanol (0.01%), heavier products (6.46%), hexane (80.07%). This corresponds to a 2-methyl-2-pentenal conversion of 98% and a selectivity of over 99% to the saturated aldehyde (2-methylpentanal).

EXAMPLE 15

Selective Hydrogenation of 2-methyl-2-pentenal to 2-methyloentanal without Solvent An autoclave, equipped with a catalyst basket fitting along the autoclave wall, was charged with 73 g of a commercial granular palladium catalyst supported on active carbon (0.5% Pd). Into the autoclave was added 990 g of an aldolization product of propanal (crude 2-methyl-2-pentenal). The aldolization product was obtained according to the procedure described in Example 14. The composition of this mixture, as determined by gas-liquid chromatography was: propanal (0.19%), 2-methyl-2-pentenal (69.14%), heavier products (30.67%). The product was hydrogenated under 1.1 MPa hydrogen pressure at 100° C.

After 290 minutes, the liquid product was drained from the reactor. The composition was: propanal (0.25%), 2-methyl-2-pentenal (1.55%), 2-methylpentanal (63.00%), 2-methylpentanol (0.43%), heavier products (34.77%). This corresponds to a 2-methyl-2-pentenal conversion of 97.8%.

EXAMPLE 16

Direct Trimer Production using NaOH Catalyst

Into a 300 ml autoclave were added 104.9 g (1.8 mol) of propanal and 5.52 g (0.039 mole) decane. The mixture was heated with stirring to 146° C., and then 66.7 g of a molar aqueous NaOH solution were added. The temperature rose to 158° C. upon addition of the NaOH solution. Heating was continued until the temperature reached 180° C., and then the temperature was maintained at 180° C. After one hour, the reaction mixture was sampled and analysed by GC. The reaction mixture contained: propanal (1.45%), $C_3$ by-products (0.8%), 2-methyl-2-pentenal (41.49%), decane (6.94%), $C_9$ unsaturated aldehydes (16.06%) and heavies (33.27%).

EXAMPLE 17

Direct Trimer Production using $TiO_2$ Catalyst

Into a 300 ml autoclave with an internal catalyst basket were loaded 37.4 g of $TiO_2$ extrudates, 87.0 g propanal, and 8.83g decane. The reactor was heated to 220° C. in 35 minutes. Over the next 55 minutes, 87.0 g propanal were added at a volumetric rate of approximately 0.5 ml/minute. After a total reaction time of three hours, the reactor was sampled and the following composition was obtained by GC: propanal (1.85%), $C_3$ by-products (0.80%), 2-methyl-2-pentenal (32.39%), decane (6.27%), unsaturated $C_9$ aldehydes (29.36%) and heavies (29.35%).

EXAMPLE 18

Production of $C_9$ Aldehydes from Propanal in a Single Reactor

Into a 300 ml autoclave were added 80 g of a molar aqueous sodium hydroxide solution and 20 g of 2% palladium on 2 mm carbon extrudates. The catalysts were heated to 125° C. under 2.1 MPa hydrogen pressure. At 125° C., with constant hydrogen pressure, the propanal plus nonane (internal standard) were introduced at a rate of 1.03 ml/minute. A total of 124.78 g (2.15 mole) propanal and 3.59 g (0.028 mole) nonane were added. A sample of the reaction mixture was removed for GC analysis after complete addition (155 minutes). The upper, organic, phase contained: 0.24% propanal, 0.35% propanol, 4.89% 2-methyl-2-pentenal, 36.03% 2-methylpentanal, 0.01% 2-methyl-2-pentenol, 4.49% 2-methylpentanol, 19.88% 2,4-dimethylheptanal, 28.38% 2,4-dimethyl-2-heptenal, 0.96% 2,4-dimethylheptanol, 0.11% 2,4-dimethyl-2,4-heptadienal, and 4.66% heavies.

Example 19

Full Hydrogenation of $C_9$ Aldehyde to 2.4-dimethylheptanol

The $C_9$ product of propanal condensation at 180° C. with a molar solution of NaOH was distilled under vacuum to yield 2-methyl-2-pentenal (0.1%), 2,4-dimethyl-2-heptanal (2.3%), 2,4-dimethyl-2,4-heptadienal (92.78%), $C_9$ by-products (3.17%) and heavies (1.65%).

Into a catalyst basket were placed 34.5 g of 16.0% nickel on alumina catalyst. The basket was inserted into a 300 ml and 160 g of the distillate identified above (containing 148.45 g (1.074 mole) of 2,4-dimethyl-2,4-hepetadienal and 19.46 g (1 mole) of cyclohexane were added. The reaction mixture was heated to 130° C. under 2 MPa hydrogen pressure.

After being maintained at constant temperature and hydrogen pressure for 40 hours, the reaction mixture was found to contain 120.3 g (0.834 mole) of 2,4-dimethylheptanol (identity confirmed by IR and NMR analysis) a yield of 77.65%.

Infra-red absorption peaks occur at the following wavenumber: 3343.4, 2956.7, 2925.8, 2872.8, 1460.0, 1379.0 and $cm^{31\ 1}$.

$C_{13}$ NMR Results for 2.4-dimethylheptanol

| Carbon Assignment | Chemical Shifts (ppm) |
| --- | --- |
| 1 | 68.43, 67.83 |
| 2 | 33.02 |
| 3 | 41.11, 40.62 |
| 4 | 29.69, 29.54 |
| 5 | 40.22, 38.88 |
| 6 | 19.98, 19.83 |
| 7 | 14.21 |
| 8 (2-methyl) | 20.21, 19.18 |
| 9 (4-methyl) | 17.22, 16.23 |

Multiple assignments are from different stereoisomers.

(b) In a similar manner, a product obtained as described in Example 12 and containing 1.1% light fraction, 92.0% 2,4-methyl-2-heptenal and 6.9% heavy fraction, was charged to an autoclave containing a basket carrying 290 g of a 50% nickel on silica catalyst, and heated to 140° C. under nitrogen. Hydrogen at 0.54 MPa was admitted to the autoclave, and the progress of hydrogenation was followed by GLC analysis of samples taken at intervals after hydrogen charging. The results are shown in Table 5 below.

TABLE 5

| Time (minutes) | 2,4-dimethyl-2-heptenal, % | 2,4-dimethyl heptanal, % | 2,4-dimethyl heptanol, % |
| --- | --- | --- | --- |
| 0 | 92.0 | 0.0 | 0.0 |
| 10 | 30.2 | 31.4 | 24.5 |
| 20 | 4.2 | 25.9 | 54.0 |
| 30 | 0.7 | 4.3 | 79.6 |
| 60 | 0.5 | 0.5 | 87.2 |

After 240 minutes, the liquid product was analysed. It contained: $C_6$ and below 2.2%, 2,4-dimethyl-2-heptenal 3.1% 2,4-dimethylheptanal 0.5%, 2,4-dimethylheptanol 85.6% heavies 8.6%.

Part C—Ester Manufacture and Use

EXAMPLE 20 production of Phthalate di-ester of 2.4-dimethylheptanol

Into a 2 liter flask were placed 473.8 g (3.28 mole) of 2,4-dimethylheptanol, 203 g (1.37 moles) of phthalic anhydride, and 0.55 g (0.00193 moles) tetraisopropoxyl titanium. The flask was heated to 220° C. for 205 minutes with stirring and nitrogen purge. The pressure was controlled between 26 and 80 kPa. At the end of the reaction, 99.92% of the phthalic anhydride had reacted. The product was treated with 0.68 g carbon and 27 g of 1% aqueous $Na_2CO_3$ for 1 hour at 90° C., dried under vacuum and filtered. Unreacted alcohol was then removed by steam stripping. The yield was approximately 540 g of bis-(2,4-dimethylheptyl)phthalate.

Infra-red absorption peaks occur at the following wavenumbers: 3438; 2800 to 3000 (broad), 1732, 1600, 1580, 1465, 1378, 1274, 1123, 1070, 1040, 970, 735, 708 and 647 $cm^{-1}$.

EXAMPLE 21

The qualities of the product of Example 20 as a plasticizer in poly(vinyl chloride) were examined.

Composition A contained 100 parts Geon 30 (a dry blend grade pvc); 50 parts phthalate ester, 2 parts stabilizer and 0.25 parts stearic acid as lubricant. This composition was blended, milled at 166° C. and molded into test samples at 171° C.

Composition B contained 100 parts Geon 121 (a plastisol grade pvc); 70 parts phthalate ester; and 2 parts stabilizer. This plastisol composition was de-aerated, gelled for 45 seconds at 150° C., and pressed into test samples at 171° C.

Properties of the test samples are set out in Table 6 below.

TABLE 6

|  | A | B |
| --- | --- | --- |
| Durometer Hardness | 85.9 | 72.0 |
| 100% modulus, $MN/m^2$ | 12.41 | 6.78 |
| Tensile Strength $MN/m^2$ | 20.7 | 16.34 |
| Clash-Berg Temp, ° C. | -22.3 | -37.5 |
| Brittleness Temp, ° C. | -27.7 | -38.0 |
| Weight Loss, 7 days at 100° C., % | 7.5 | 8.9 |
| Plastisol Viscosity, Pas at 39.7 $sec^{-1}$ | 4.15 | 4.24 |

EXAMPLE 22

Production of the Trimellitate Ester of 2 4-dimethylheptanol

Into a 2 liter flask were placed 340 g 2,4-dimethylheptanol, 125.9 g of trimellitic anhydride, and 0.33 g tetraisopropoxyl titanium. After purging and degassing by nitrogen purge and vacuum, the flask was heated to 218° C. for 3 hours under reduced pressure (32 kPa). At the end of the reaction period, 99.92% of the trimellitic anhydride had been converted. The heat source was removed and the reaction mixture was slowly cooled while maintaining vacuum. When the reaction mixture reached 90° C., the vacuum was released and a mixture of charcoal (amount equal to 0.16% of product weight) and sodium carbonate (amount equal to twice the stoichiometry) with 2 wt % of distilled water was added with constant stirring. A vacuum was again applied, with the pressure slowly reduced over 20 minutes to 13 kPa to remove the water from the reaction mixture. The sample was filtered through dicalite and unreacted alcohol removed by steam stripping. The yield was approximately 286g of tris-(2,4-dimethylheptyl) trimellitate.

Infra-red absorption peaks occur at the following wavenumbers ($cm^{-1}$):

| 752 | 981 | 1066 | 1114 | 1240 | 1282 | 1302 | 1379 |
| --- | --- | --- | --- | --- | --- | --- | --- |
| 1410 | 1465 | 1491 | 1730 | 2847 | 2928 | 2955 | | specific gravity at 15.6° C.: 0.978

EXAMPLE 23

The qualities of the product of Example 22 as a plasticizer in poly (vinyl chloride) were examined. Composition C. contained 100 parts Geon 30, 52 parts trimellitate ester, 10 parts stabilizer (dibasic lead phthalate) and 7 parts clay filler. The composition was evaluated for dry blending time by the procedure of ASTM 2396 (Recommended Practice for Powder-Mix Test of PVC using a Torque Rheometer). The trimellitate ester of Example 22 gave a dry blend time of 10 minutes typical of that observed for commercial trimellitate esters.

EXAMPLE 24

In this Example, composition D was prepared employing 100 parts of Geon 30, 40 parts trimellitate ester of Example 22, 6 parts stabilizer (coated dibasic lead phthalate) and 0.5 parts lubricant (dibasic lead sulphate). The materials were hand-mixed and then milled for 5 minutes at 175° C. The plasticized pvc was removed from the mill, cooled to room temperature and aged for 24 hours before being tested using ASTM.D257 (Standard Test Methods for DC Resistance or Conductance of Insulating Materials). The volume resistivity was $3.59 \times 10^{-8}$ ohm.cm.

EXAMPLE 25

Production of the Acetate of 2.4-dimethylheptanol

Into a 100 ml flask were placed 20g of 2,4-dimethylheptanol and 40 g of acetic anhydride. The mixture was stirred with heating at about 100° C. for 2 hours, after which the reaction mixture was slowly cooled to room temperature. 50g water were added to hydrolyse the excess acetic anhydride. The mixture was transferred to a separating funnel, washed repeatedly with a 5% aqueous sodium bicarbonate solution, then with water and dried over anhydrous sodium sulphate. The product was the acetate of 2,4-dimethylheptanol. Isolated product yield was in excess of 95%.

Infra-red absorption peaks occur at the following wavenumbers ($cm^{-1}$):
1035 1238 1365 1377 1465 1743 2847 2930 2959
specific gravity at 15.6° C.: 0.8718
Boiling range (determined by simulated GC distillation): 213 to 225° C.

Aroma profile testing of the ester showed a strong floral character, with citrus and terpene overtones.

What is claimed is:

1. A composition comprising a $C_6$ aldehyde and a saturated aliphatic $C_9$ aldehyde made by subjecting a saturated $C_6$ aldehyde to an aldol condensation with propanal to form a product comprising an unsated $C_9$ aldehyde, and hydrogenating the unsaturated aldehyde to a saturated $C_9$ aldehyde, wherein said composition contains greater than 35 percent $C_9$ aldehydes on a $C_9$ and higher aldehyde basis.

2. A composition as claimed in claim 1, wherein said $C_6$ aldehyde is 2-methylpentanal and said saturated aliphatic $C_9$ aldehyde is 2,4-dimethylhcptanal.

3. An ester formed from 2,4dimethylheptanol, other than a mixed ester of 1,2-benzenedicarboxylic acid with said 2,4dimethylheptanol and a saturated $C_8$, $C_9$ or $C_{10}$ primary alkanol.

4. A plasticizer composition comprising an ester made from a polybasic acid and an alkanol blend, said alkanol blend comprising at least 50 percent of 2,4-dimethylheptanol and less than 50 percent of a compound selected from the group consisting of 2-methylpentanol, 2,4,6-trimethylnonanol, and combinations thereof.

5. A plasticizer composition comprising an ester made from a polybasic acid and an alkanol blend other than a plasticizer composition consisting of the mixed ester of 2,4-dimethylheptyl and 4,6-dimethylheptyl alcohols with 1,2-benzenedicarboxylic acid, said alkanol blend comprising at least 5 percent by weight of 2,4dimethylheptanol and correspondingly at most 95 percent by weight of another alkanol or alkanols having from 6 to 12 carbon atoms.

6. A polymeric composition comprising a polymer and a plasticizer composition as claimed in claim 5.

7. A refrigerant fluid comprising:
as a lubricant component, an ester formed from 2,4-dimethylheptanoic acid and an alcohol containing two or more carbon atoms other than a tetraester of pentaerythritol 2-methyl-hexanoic acid and 2,4-dimethylheptanoic acid;
wherein said ester is not a polyol ester, wherein each hydroxyl group of the polyol is esterified by an acid selected from 2,4-dimethylheptanoic acid and 2,4,6-trimethylnonanoic acid.

8. A synthetic lubricant, comprising:
an ester of 2,4dimethylheptanoic acid and an alcohol containing two or more carbon atoms other than a tetraester of pentaerythritol 2-methyl-hexanoic acid and 2,4-dimethylheptanoic acid; and
wherein said synthetic lubricant is not a fluorocarbon refrigerant oil lubricating composition comprising a polyol ester, wherein each hydroxyl group of the polyol is esterified by an acid selected from 2,4-dimethylheptanoic acid and 2,4,-trimethylnonanoic acid.

9. An ester formed from 2,4dimethylheptanoic acid and an alcohol, wherein said alcohol contains at least two carbon atoms and only one hydroxyl group.

10. An ester formed from 2,4-dimethylheptanoic acid and an alcohol other than a tetraester of pentaerythritol, 2-methyl-hexanoic acid and 2,4dimethylheptanoic acid;
wherein said alcohol contains at least two carbon atoms and two or more hydroxyl groups; and
said ester is not a polyol ester, wherein each hydroxyl group of the polyol is esterified by an acid selected from 2,4-dimethylheptanoic acid and 2,4,-trimethylnonanoic acid.

11. An ester formed from 2,4-dimethylheptanol, other than a mixed ester formed from 1,2-benzenedicarboxylic acid, said 2,4dimethylheptanol and a compound selected from the group consisting of $C_8$ primary alcohols, $C_9$ primary alcohols other than said 2,4-dimethylheptanol, and $C_{10}$ primary alcohols.

12. An ester as claimed in claim 11, wherein said ester is formed from a dibasic acid and said 2,4-dimethylheptanol.

13. An ester as claimed in claim 11, wherein said ester is selected from the bis (2,4-dimethylheptyl) esters of 1,2-benzenedicarboxylic and hexanedioic acids and the tris (2,4-dimethylheptyl) ester of 1,2,4-benzenetricarboxylic acid.

14. An ester as claimed in claim 11, wherein said ester is 2,4-dimethylheptyl acetate.

15. An ester as claimed in claim 11, wherein said ester is formed from a polybasic acid and an alcohol mixture, wherein said alcohol mixture contains at least 50 percent of 2,4-dimethylheptanol and less than 50 percent of other alcohols.

16. A mixture comprising an ester, wherein said ester is formed from an alcohol mixture containing greater that 5 percent by weight of 2,4-dimethylheptanol.

17. A mixture as claimed in claim 16, wherein said alcohol mixture contains greater than 50 percent by weight of 2,4dimethylheptanol.

18. A mixture comprising an ester as claimed in claim 16, wherein said ester is formed from a dibasic acid and said alcohol mixture.

19. A mixture comprising an ester as claimed in claim 17, wherein said ester is formed from a dibasic acid and said alcohol mixture.

20. A mixture comprising an ester as claimed in claim 16, wherein said ester is selected from the bis (2,4-dimethylheptyl) esters of 1,2-benzenedicarboxylic and hexanedioic acids and the tris (2,4dimethylheptyl) ester of 1,2,4-benzenetricarboxylic acid.

21. A mixture comprising an ester as claimed in claim 17, wherein said ester is selected from the bis (2,dimethylheptyl) esters of 1,2-benzenetricarboxylic and hexanedioic acids and the tris (2,4-dimethylheptyl) ester of 1,2,4-benzenetricarboxylic acid.

22. A mixture comprising an ester as claimed in claim 16, wherein said ester is 2,4-dimethylheptyl acetate.

23. A mixture comprising an ester as claimed in claim 17, wherein said ester is 2,4-dimethylheptyl acetate.

* * * * *